(12) United States Patent
Kovanen

(10) Patent No.: US 12,415,087 B1
(45) Date of Patent: Sep. 16, 2025

(54) MAGNETIC PULSE THERAPY DEVICE (MPTD) WITH DYNAMIC DIRECTIONAL FLUX CONTROL

(71) Applicant: Innovator Corporation, Browns Point, WA (US)

(72) Inventor: David Kovanen, Browns Point, WA (US)

(73) Assignee: Innovator Corporation, Browns Point, WA (US)

( * ) Notice: Subject to any disclaimer, the term of this patent is extended or adjusted under 35 U.S.C. 154(b) by 0 days.

(21) Appl. No.: 19/072,219

(22) Filed: Mar. 6, 2025

Related U.S. Application Data

(63) Continuation-in-part of application No. 18/905,994, filed on Oct. 3, 2024, which is a continuation of application No. 18/432,044, filed on Feb. 4, 2024, now Pat. No. 12,268,891.

(51) Int. Cl.
*A61N 2/02* (2006.01)
*A61N 2/00* (2006.01)

(52) U.S. Cl.
CPC .............. *A61N 2/02* (2013.01); *A61N 2/008* (2013.01)

(58) Field of Classification Search
CPC .................................. A61N 2/008; A61N 2/02
See application file for complete search history.

(56) References Cited

U.S. PATENT DOCUMENTS

| | | | | |
|---|---|---|---|---|
| 4,757,804 A | * | 7/1988 | Griffith | A61N 2/02 607/51 |
| 6,132,362 A | | 10/2000 | Tepper | |
| 9,849,302 B1 | * | 12/2017 | Fischell | A43B 7/00 |
| 2002/0151760 A1 | * | 10/2002 | Paturu | A61N 2/02 600/15 |
| 2003/0158585 A1 | | 8/2003 | Burnett | |
| 2014/0249354 A1 | | 9/2014 | Anderson | |
| 2015/0375005 A1 | * | 12/2015 | Segal | A61N 2/006 600/13 |

FOREIGN PATENT DOCUMENTS

| CN | 112494815 A | 3/2021 |
|---|---|---|
| CN | 216319524 U | 4/2022 |

* cited by examiner

*Primary Examiner* — Carrie R Dorna
*Assistant Examiner* — Joshua Daryl D Lannu
(74) *Attorney, Agent, or Firm* — Stevens Patent Law LLC; Dat Mai

(57) ABSTRACT

A Magnetic Pulse Therapy Device (MPTD) configured to deliver dynamically oriented magnetic flux using a fixed applicator. The device includes a segmented solenoid with independently controlled coils arranged circumferentially around a treatment zone. Energizing specific solenoid segments with opposite polarities creates points of opposition, while leaving gaps between opposing segments allows flux to escape. The escaping flux can be oriented up to 90° from the core's longitudinal flux direction within the solenoid. This controlled flux manipulation enhances therapeutic effectiveness compared to conventional bipolar core flux. The device is suitable for both clinical and home applications.

30 Claims, 18 Drawing Sheets

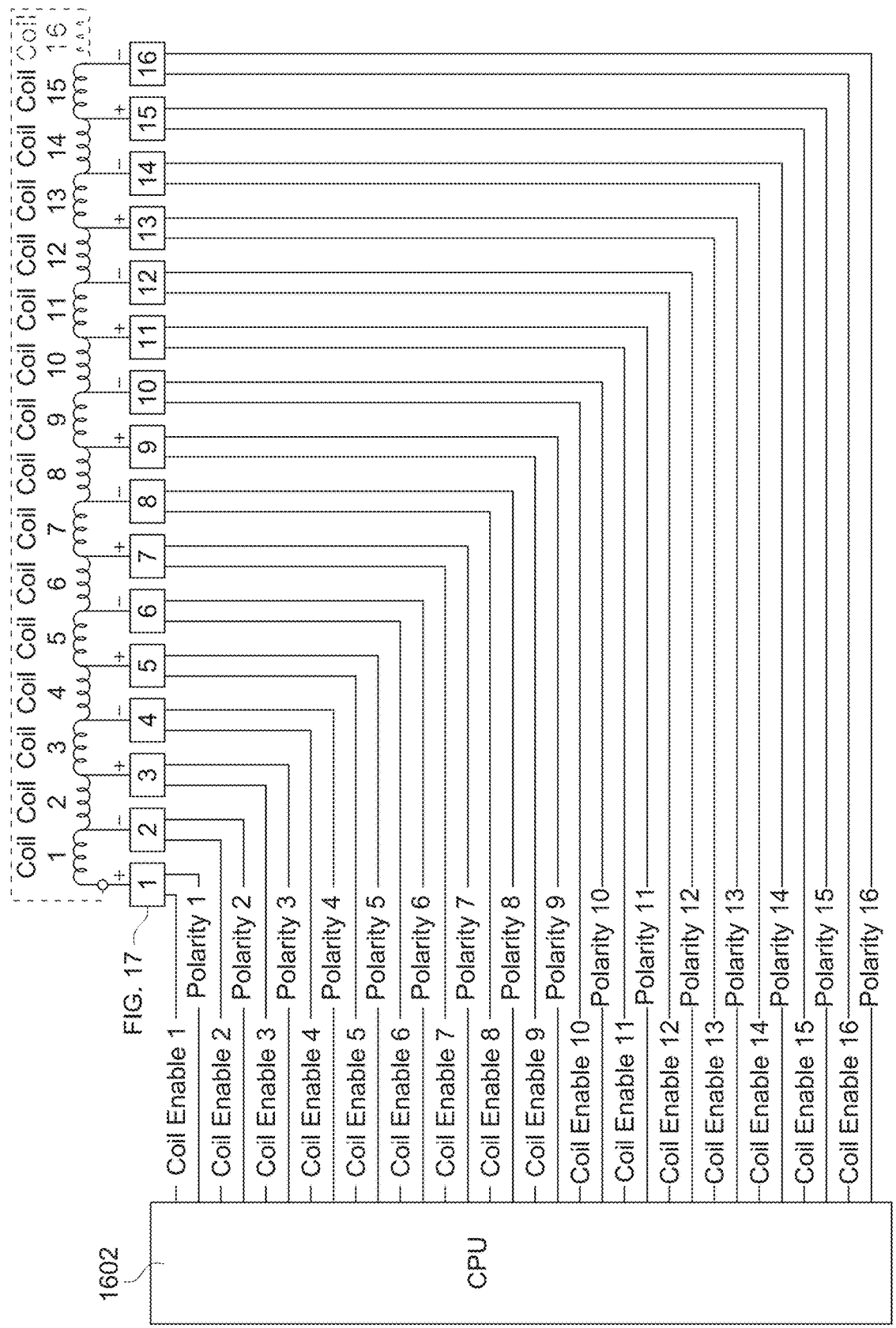

MAGNETIC PULSE THERAPY DEVICE (MPTD) WITH DYNAMIC DIRECTIONAL FLUX CONTROL

CROSS REFERENCE TO RELATED APPLICATIONS

| Application No. | Date Filed | Title |
|---|---|---|
| Current application | Herewith | Magnetic Pulse Therapy Device (MPTD) with Dynamic Directional Flux Control |
| | | Is a continuation-in-part of: |
| 18/905,994 | Oct. 3, 2024 | Magnetic Pulse Therapy Device (MPTD) for the Treatment of Pain |
| | | Is a continuation of: |
| 18/432,044 | Feb. 4, 2024 | Magnetic Pulse Therapy Device (MPTD) for the Treatment of Pain | the entire specification of each of which is incorporated herein by reference.

TECHNICAL FIELD OF THE INVENTION

This disclosure relates to the field of medical devices, specifically magnetic pulse therapy devices (MPTDs).

DISCUSSION OF THE STATE OF THE ART

Magnetic Pulse Therapy Devices (MPTDs) have demonstrated significant therapeutic potential, particularly for neuropathic pain treatment. A breakthrough in MPTD technology was achieved in the parent application through a novel segmented solenoid design that enables safe, home-based treatment at low voltages while delivering therapeutically effective magnetic flux levels.

A feature of solenoid-based therapeutic magnetic devices is that they primarily utilize core flux, which is limited by a fixed longitudinal orientation along the solenoid's axis. While these devices can provide consistent, thorough, and high-quality coherent flux to large treatment areas, the magnetic flux maintains only a positive or negative polarity in either 0° or 180° axial orientation.

Research in electromagnetic therapy has established that the orientation of magnetic flux relative to cellular structures and nerve pathways significantly impacts therapeutic efficacy. This understanding is grounded in fundamental principles of electromagnetic induction and cellular biology. When nerve cell membranes with embedded ion channels are exposed to magnetic flux, the induced electrical effects depend not only on the rate of change of the magnetic field but also on the orientation of flux lines relative to cellular structures.

Manually operated applicators are not solenoid-based and they can deliver flux at various orientations as manipulated by clinicians. They also provide non-core flux that is multi-axial and more randomized. This non-core flux exhibits high spatial and directional dispersion with a stochastic, multi-axial distribution lacking dominant orientation, ensuring broader interaction with cellular components and potentially delivering superior therapeutic outcomes compared to single-axis coherent fields from solenoid core flux.

SUMMARY OF THE INVENTION

The present application introduces Dynamic Directional Flux Control (DDFC) to a solenoid based Magnetic Pulse Therapy Device (MPTD). This DDFC offers the best of both solenoid-based and handheld applicator MPTDs. With DDFC, magnetic pulses can be produced with flux having a variety of axial orientations in a repeatable, reliable way, using a simple device suitable for in-home use, without the need for assistance by others.

With a solenoid based MPTD, a foot is slid into the solenoid and the foot is treated concurrently with bipolar magnetic pulses from the core of the solenoid. But with DDFC, the orientation of the flux is directed in any number of directions with almost 360° possible in all three axis. This advanced MPTD system with DDFC enables real-time, precision control of magnetic flux orientation throughout the treatment zone.

The DDFC mechanism operates through selective activation and polarity modulation of individual coil segments within the segmented solenoid. The exact flux re-orientation point is dictated by points of polarity inversion within the solenoid segments. ("points of opposition") The angle and intensity of re-oriented flux at the point of opposition are dynamically controlled by strategic non-energization of specific solenoid segments at or near the points of opposition, which modifies local reluctance pathways to facilitate precise field steering.

In an idealized segmented solenoid configuration, polarity inversion where there is no gap at the point of opposition would primarily induce flux cancellation at the point of opposition. To counteract this, strategic non-energization of selected solenoid segments near the point of opposition is employed. This approach exploits the inherent magnetic reluctance properties of the core flux within the segmented solenoid, compelling the flux to redirect perpendicularly through the gaps at the point of opposition.

The DDFC mechanism can be analogized to two opposing high-pressure fluid jets. If the jets meet with zero separation, the opposing forces cancel, preventing lateral flow. However, introducing a controlled gap at the point of opposition forces the fluid to eject approximately perpendicularly. Varying the gap influences the intensity and distribution of the perpendicular flow.

This reluctance-induced flux displacement enables dynamic redirection of the magnetic field, with orientation that is finely controlled through individual solenoid segment activation. Deactivation of solenoid segments at or near the point of opposition strategically modifies reluctance pathways, enabling and controlling perpendicular flux channels within the treatment zone.

In practice, DDFC is both remarkably simple and inexpensive. A typical segmented solenoid based mid-power MPTD may have four (4) to twenty (23) segments. In the parent application it is disclosed that one or more solenoid segments may be energized with the same polarity, most commonly all of the solenoids encircling the inserted appendage to be treated will be energized with the same polarity to create core flux. The polarity may be reversed periodically to create a bipolar magnetic pulse with axial orientations of 0° and 180°.

To create oriented flux, a point of opposition is selected. One or more segments at this point of opposition will be left de-energized. The coils to one side of the point of opposition will all be energized with one polarity and the coils on the opposing side will be concurrently energized with the opposite polarity. The result will be flux flowing through the gap left by the non-energized segment or segments at orientations up to 90°. Another possibility is to physically space the segments slightly apart from each other so as to have adequate gaps between them and in this case it is possible for all segments to be energized with the physical inter-segment gaps serving as the escape route for flux.

The point of opposition can be relocated and re-sized between each pulse or even during an ongoing pulse. That is, altering the point of opposition and the gap size can dynamically alter the flux both between pulses and within pulses.

The DDFC can be controlled with higher precision by having a larger number of segments in the solenoid. It can also be controlled by individually varying the energy supplied to each coil within the segmented solenoid. Instead of the coils at the points of opposition being fully un-powered, these coils can be weakly powered so as to vary the flux path and angle. It is directly analogous to one of the opposing jets turning down its pressure so that the opposing jet overpowers it, bending back the flow towards the weaker jet.

Such energy control can be accomplished both by varying the voltage or current and also through techniques such as Pulse Width Modulation (PWM). Time modulating the power of coils in the gap can "spray" magnetic flux in many orientations in the gap area, much like an oscillating lawn sprinkler.

BRIEF DESCRIPTION OF THE DRAWINGS

FIG. 16 shows the central processing unit 1602, general wiring configuration, and a control block (further illustrated in FIG. 17).

DETAILED DESCRIPTION

Definitions

Figure 1:
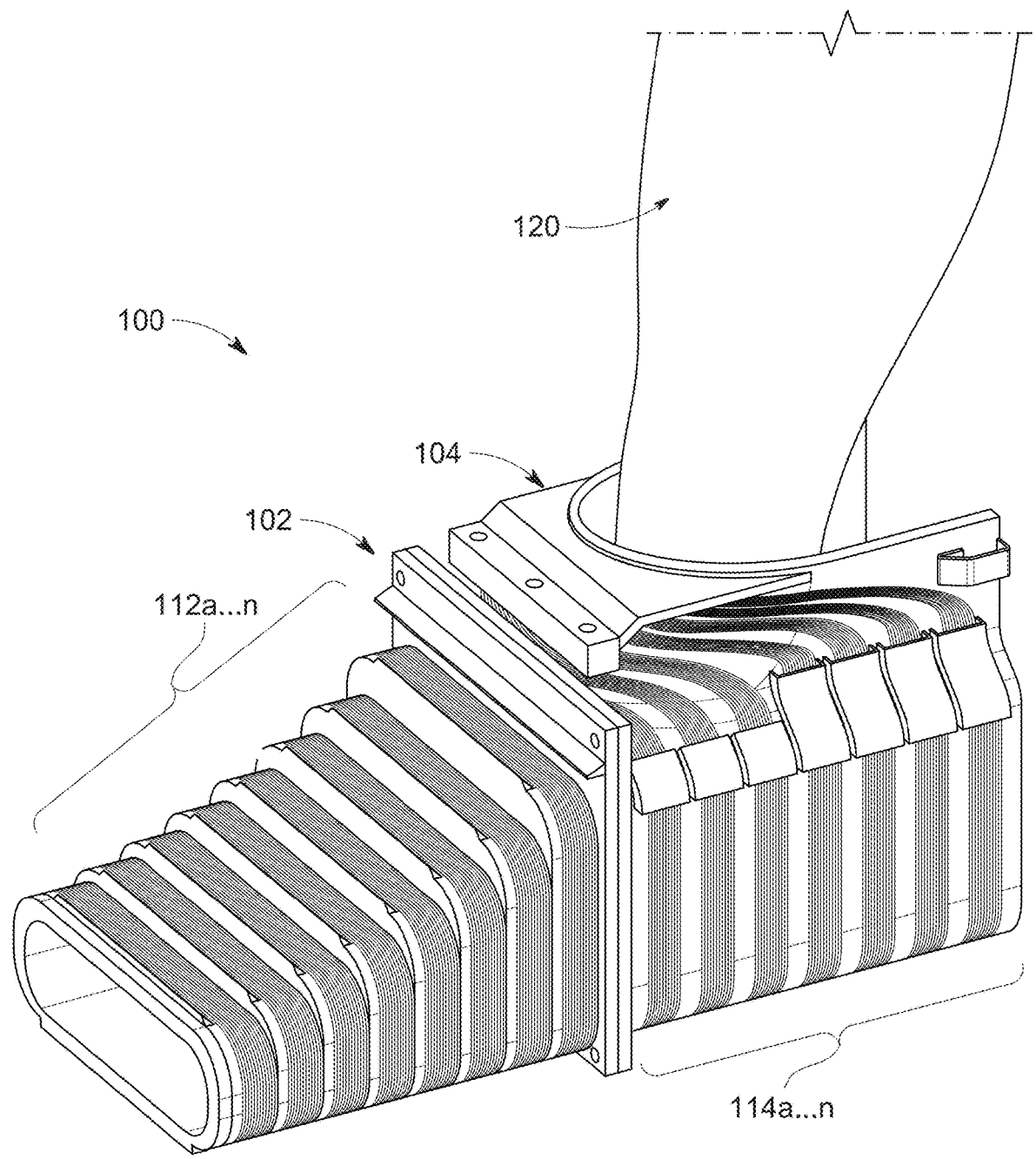
FIG. 1 is a perspective view illustrating a Magnetic Pulse Therapy Device (MPTD) applicator 100, showing the forefoot section 102 and hindfoot section 104 with their respective independently controllable coils 112a ... n, 114a ... n positioned to receive an appendage 120.

Throughout this specification, where reference elements are denoted with letters "a ... n", "n" represents a positive integer denoting the final element in a series of one or more related components. While specific embodiments may illustrate a particular number of elements (e.g., six widgets labeled 006a ... n), it should be understood that this quantity is exemplary, and implementations may include any practical number of such elements, limited only by physical and engineering constraints of the system.

The illustrated embodiment in the drawings is designed to treat all or a portion of a human foot and the illustrations are optimized for this embodiment. But where "foot" is used, it should be understood to mean any appendage, such as a hand, or even both feet.

The term "segmented solenoid" in this application means a solenoid comprised of a multiplicity of coils ("segments") which are physically configured such that when energized the flux produced by them interacts in an intentional way, often involving magnetic coupling. Traditionally, when all coils are energized, they would produce flux with the same axial orientation, creating an operative solenoid with core flux. For the present application the term is to be somewhat more fluid than the traditional meaning, since segments may be intentionally energized to produce opposing core flux, or they may even be left un-energized so as to leave gaps through which flux may escape. The determination of whether coils form a segmented solenoid is more based on the intentional cooperation of these coils to achieve a flux orientation goal.

The term "coil", as before, is one or more windings, each with a multiplicity of turns, which are controlled and powered (energized) together. It is immaterial how the windings are configured, and they may be wired in series or parallel and may be in close proximity or far from each other. By definition, a coil has one power wire on each extremity and its windings are controlled and powered as a unit.

The term "winding" is a wrapping (turn) of a segment of one continuous wire around a core (such as an air core). This is a contextual term because multiple windings wired in series could be referred to as a single winding or as multiple windings wired in series. The term "winding" therefore means only a piece of wound wire and does not describe its role within the coil that it is a part of.

The terms "turn", "wrap", "wrapping" or "loop" all mean one circumferential encircling around a core, such as an air core of a coil or solenoid.

A "solenoid" is one or more coils which together have a purposeful length and some degree of magnetic coupling. A solenoid may consist of a single winding around a core for a meaningful and purposeful length or may have a variety of winding structures and coil arrangements. The term solenoid can include an "operative solenoid".

The traditional meaning of "operative solenoid" is that it is determined to exist when there is core flux within the core of a solenoid and not by any specific spacing, alignment, or shape similarities of its coils or windings. The determination of whether there is sufficient magnetic coupling of flux to form an operative solenoid is an objective standard and was defined in the original application.

For the purposes of this application the definition of "operative solenoid" needs to be expanded. A simple test is whether core flux or magnetic coupling of segments would exist if all coils in the segmented solenoid were concurrently energized. That is, it will suffice that the coils are configured in such a way that the flux interacts between these coils in purposeful ways. A solenoid where some segments are energized to oppose other segments to create perpendicular flux, or where some segments are not energized so as to leave flux gaps, will still be within the meaning of "operative solenoid" for the purposes herein.

The term "gap" refers to a configuration of a segmented solenoid where magnetic flux escapes or is ejected out of the core of the solenoid through its side wall at a point of opposition. This gap may be created by one or more coils being de-energized or weakly energized, or the gap may be a physical space between the windings of coil forming the segmented solenoid.

The terms "escape" and "eject" mean the additional flux that exits from the core of the segmented solenoid through a gap near a point of opposition. The amount of "escaping flux" or "ejected flux" is the additional amount of flux which exits near a point of opposition when compared to when there is no point of opposition. For the purposes of the present application, "escape" does not mean leakage flux that is de minimis such as may naturally flow between coils in a segmented solenoid.

The term "pulse" means the period from the start of flux generation within an operative solenoid to the end of flux generation. A single pulse may be complex and may consist of one or more polarity reversals, differing combinations of coils being energized within the segmented solenoid over a period of time, or varying power levels of all or some coils.

The term "energized" means that a coil is powered, resulting in the coil producing magnetic flux in the core of the solenoid. If a coil near a point of opposition is unpowered or is sufficiently weakly powered as to create a gap that allows flux to escape or be ejected, then it is deemed "unpowered" or "non-energized" for the purposes of this specification. That is, an unpowered or non-energized coil has its power level sufficiently weakened (such as lowering the voltage, amperage or use of pulse width modulation) so as to form or shape a gap near a point of opposition.

The term "treatment session" means the time from when an appendage is inserted into a Magnetic Pulse Therapy Device (MPTD) to the time that the appendage is removed. A single treatment session may involve starting, stopping, or altering the treatment protocol one or more times.

Device Structure

Referring to FIG. 1, an MPTD device comprises an applicator 100 with distinct forefoot 102 and hindfoot 104 sections. The applicator incorporates a segmented solenoid consisting of multiple independently controllable coils, designated as 112a . . . n in the forefoot section and 114a . . . n in the hindfoot section 104, arranged to form a treatment zone capable of receiving an appendage 120. This design enables precise control over magnetic field generation throughout each segment of the segmented solenoid, creating a treatment volume encompassing the entire appendage, in this case a foot.

Figure 2:
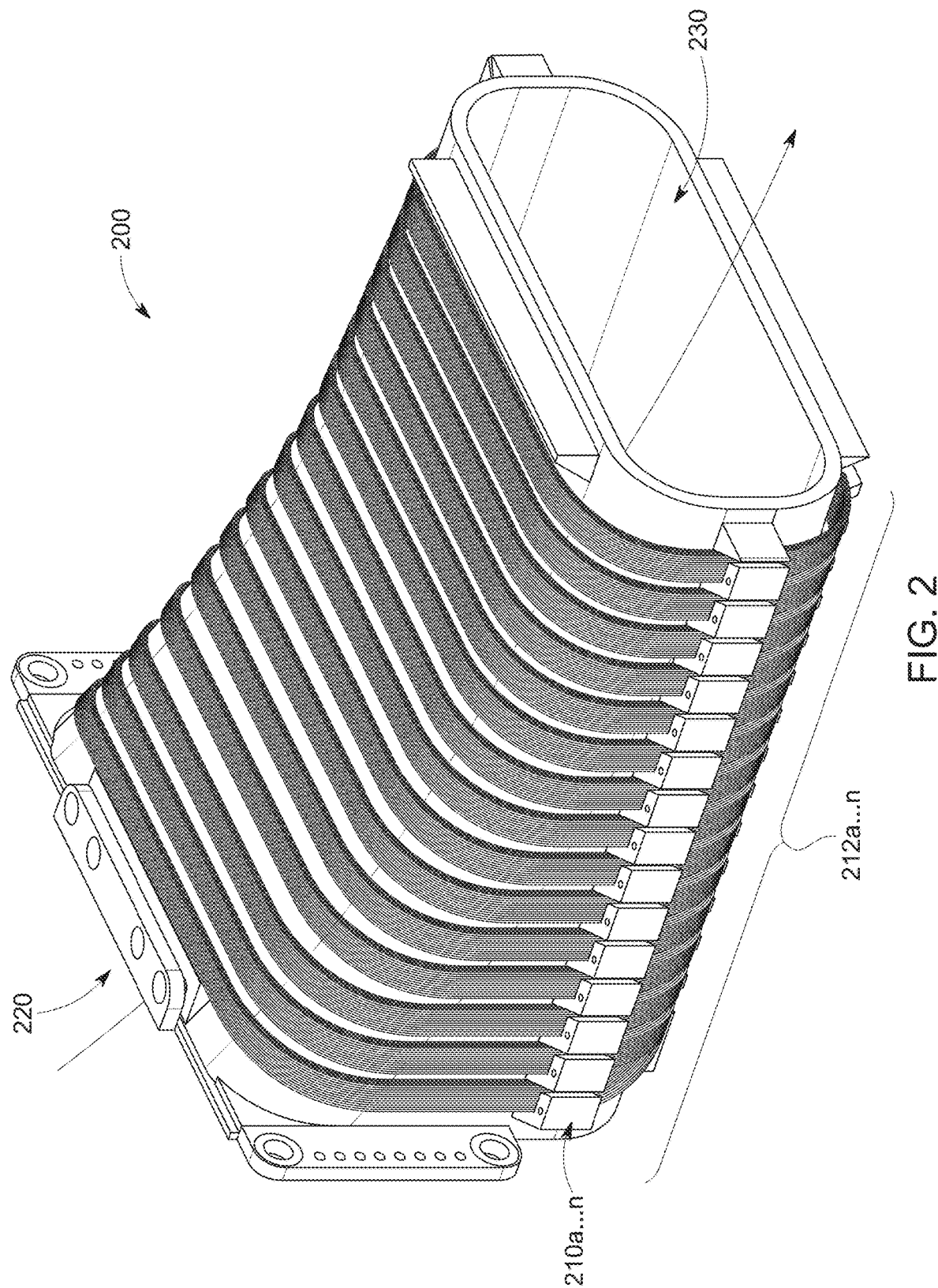
FIG. 2 shows an alternative embodiment 200 of the forefoot section FIG. 1, 102 with wire retention clips 210a ... n supporting fifteen (15) forefoot coils 212a ... n. The applicator includes a rear opening 220 and forward opening 230.

FIG. 2 illustrates an alternative embodiment 200 of the forefoot section FIG. 1, 102, demonstrating one possible integration of the structural core and electromagnetic coils. Wire retention clips 210a . . . n provide precise positioning and secure mounting for coils 212a . . . n. The applicator's design incorporates a proximal opening 220 for the distal insertion of an appendage such as a foot. The forefoot section 200 may be used independently or may be combined with a hindfoot section 104 allowing the foot to be distally inserted through the proximal opening FIG. 14A and FIG. 14B 1406, 1404. The distal opening 230 is optional and its presence of absence is immaterial to the functioning of the device.

Figure 3:
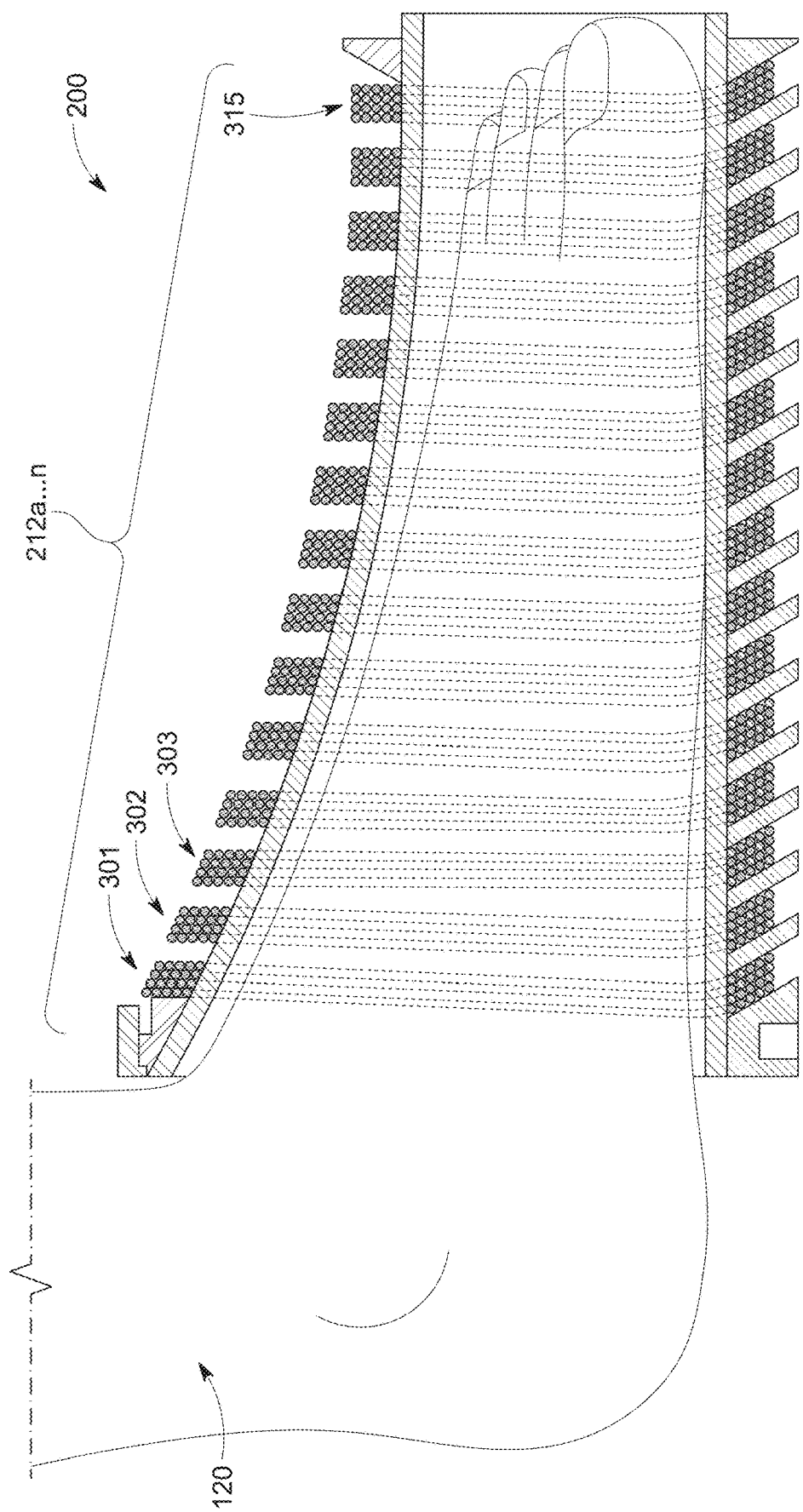
FIG. 3 shows a cross-sectional view of the forefoot section 200 with an appendage 120 positioned within coil array 212a ... n, wherein coil positions 301-315 are arranged sequentially along the array, with positions 304-314 following the established pattern between the illustrated positions.

The cross-sectional geometry of a forefoot section 200 is detailed in FIG. 3, showing the precise positioning of coils 301-315 within the forefoot section 200. The appendage 120 placement within the segmented solenoid 212a . . . n is within the core. The treatment zone extends throughout the forefoot from the proximal end 301 through the central region 308 to the distal end 315, enabling comprehensive coverage of the target tissues. Nerve bundles are generally 10 to 25 mm from the skin surface, and the contour of the core 200 results in the coils being in closer proximity to an inserted foot than if the core were a simpler shape, such as cylindrical.

Figure 4:
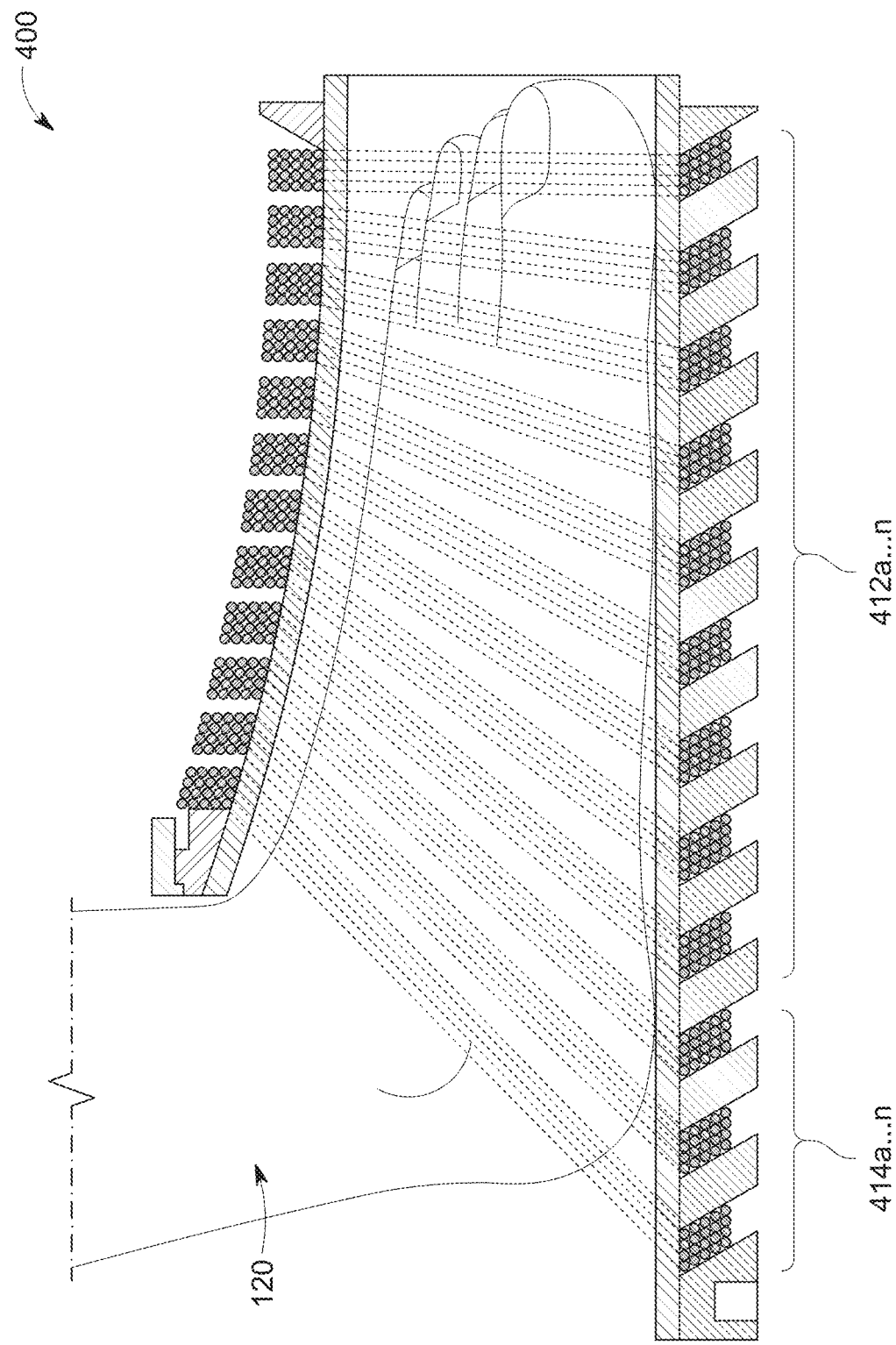
FIG. 4 illustrates an alternative "slipper" configuration 400 with independently controllable coils arranged in forefoot 412a ... n and heel 414a ... n regions around an appendage 120.

FIG. 4 presents an alternative 'slipper' configuration 400 that maintains therapeutic effectiveness while offering a different style applicator. This implementation arranges the coils in both forefoot 412a . . . n and heel 414a . . . n regions around the appendage 120, demonstrating the adaptability of the basic design principles to different therapeutic requirements. The coils at the proximal end 414a . . . n can be formed so as to be vertical and then curve to traverse around the inner ankle, so as to provide greater coverage of the ankle area, if desired. Where therapy for plantar fasciitis is the priority, the shorter and more direct route for the proximal coils (as shown) 414a . . . n would be preferable.

Figure 5:
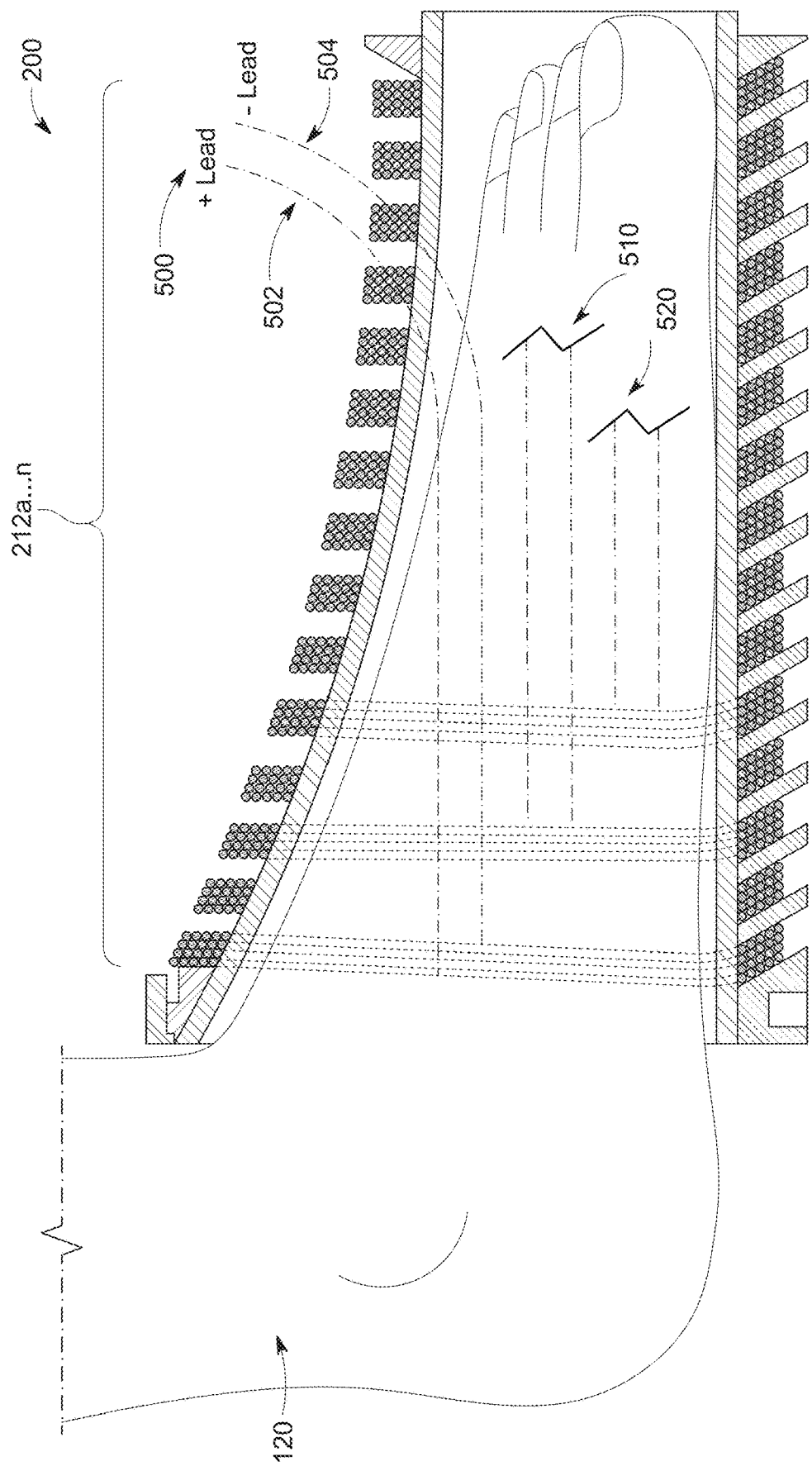
FIG. 5 demonstrates a set 500 of independent positive 502 and negative 504 leads for coil 301. Every coil 212a ... n has a set of leads. Coil leads 510, 520 for coil 303 and coil 305 are also shown as additional examples.

FIG. 5 illustrates an applicator optimized for a human forefoot with 15 coils. Each coil has a pair of wires 500, 510, 520 which allow the coil to be energized. One wire can be designated the positive lead 502 and the other lead would be the negative lead 504 but this is a naming convention only as each lead will be energized with both positive and negative voltages. The coil will produce magnetic flux provided that both leads are opposite in the polarity of voltage supplied. If the coils are wired in a half-tap configuration as shown schematically in FIG. 16, where the energizing circuitry is shared by coils, then it is optimal to either reverse the positive and negative coil leads or else wire the coil in the opposite rotation. In the half-tap configuration, if it is desired for a coil to be non-energized, while its adjacent coils were energized to produce opposite oriented flux, the non-energized coil would have both of its leads 502, 504 with the same polarity. The fact that it may have a voltage potential that is high or low is of no consequence, the coil will be non-energized.

Orienting Flux

Figure 6:
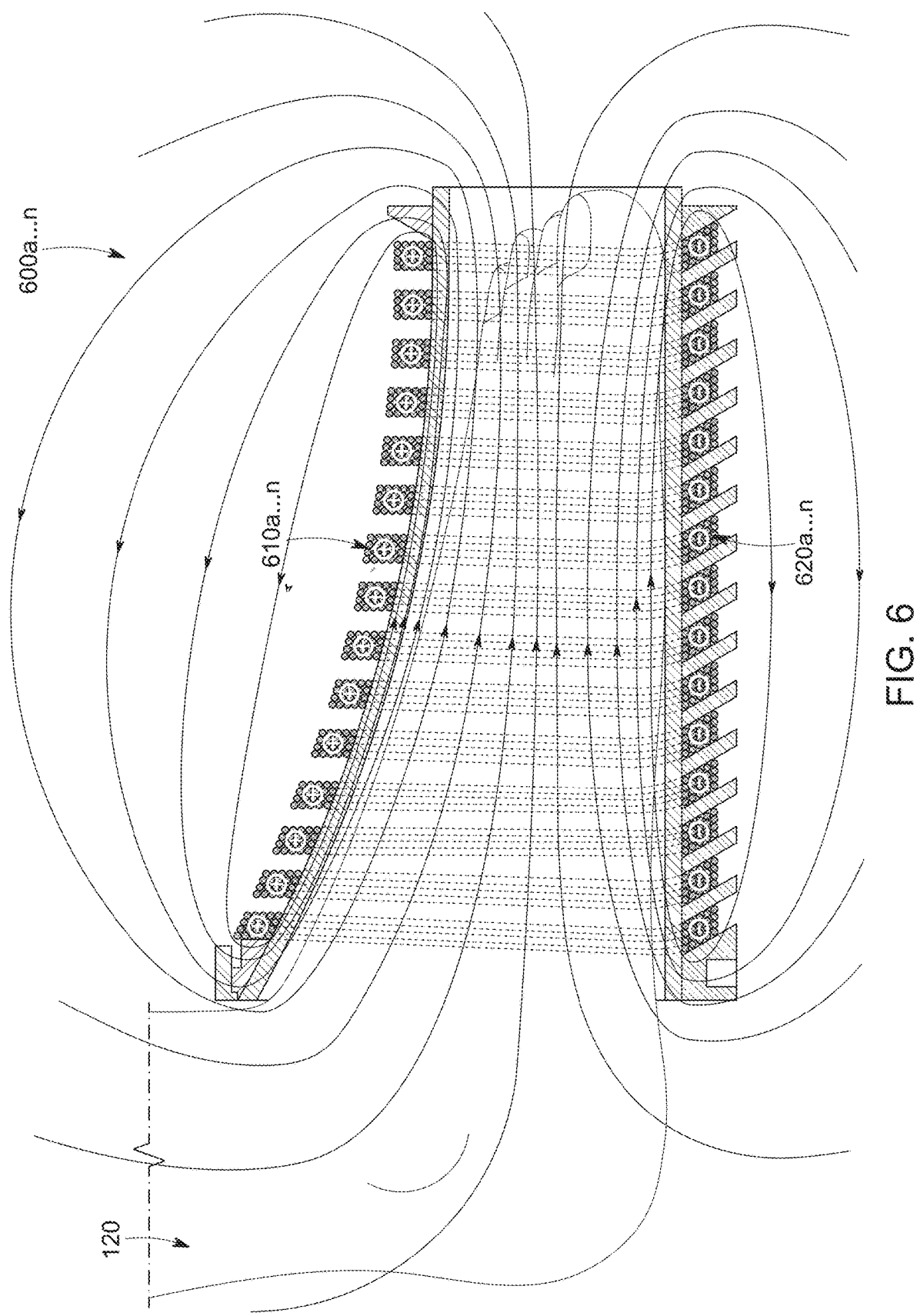
FIG. 6 illustrates the magnetic flux lines 600a ... n generated when coils of this configuration are energized with uniform polarity, showing the field pattern around an appendage 120.

A conventional segmented solenoid produces core flux that flows longitudinally through the core of the solenoid as depicted in FIG. 6 with the lines of flux illustrated as 600a . . . n. The flux is denser close to the coils 610a . . . n and 620a . . . n than it is in the center of the solenoid. While this is ideal for magnetic pulse treatment of the foot since nerves are also close to the surface, it does mean that flux travels longitudinally through the solenoid core with either a positive or negative polarity (0° or 180° axial orientations).

Figure 17:
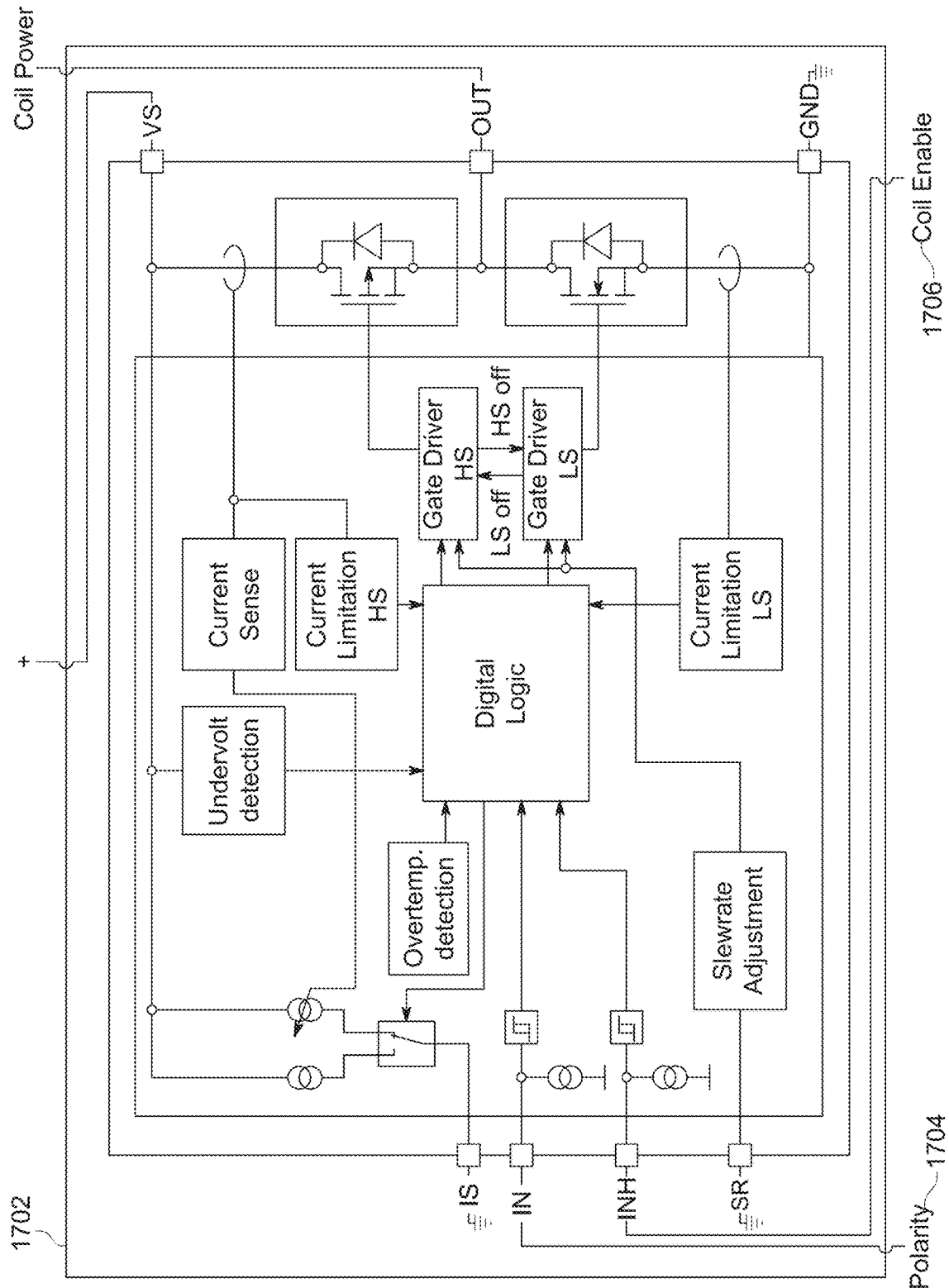
FIG. 17 illustrates the control system architecture 1702, a polarity control connection point 1704, and a coil control connection point 1706.

As shown in FIG. 5, each coil 212a . . . n in the array has independent positive 502 and negative 504 leads connected to the control circuitry FIG. 16 and FIG. 17, enabling individual control of both activation and polarity. This independent control of each coil allows the device to generate distinct flux patterns and orientations.

By selectively energizing individual coils within the segmented solenoid with different polarities the magnetic flux orientation in the sagittal, transverse, and coronal planes of an appendage being treated. Phrased differently—the system can create flux at many angles and at specific orientations relative to a treatment target. This is done by creating points of opposition of varying intensities throughout the solenoid and therefore throughout the treatment zone FIG. 7-FIG. 12.

Figure 7:
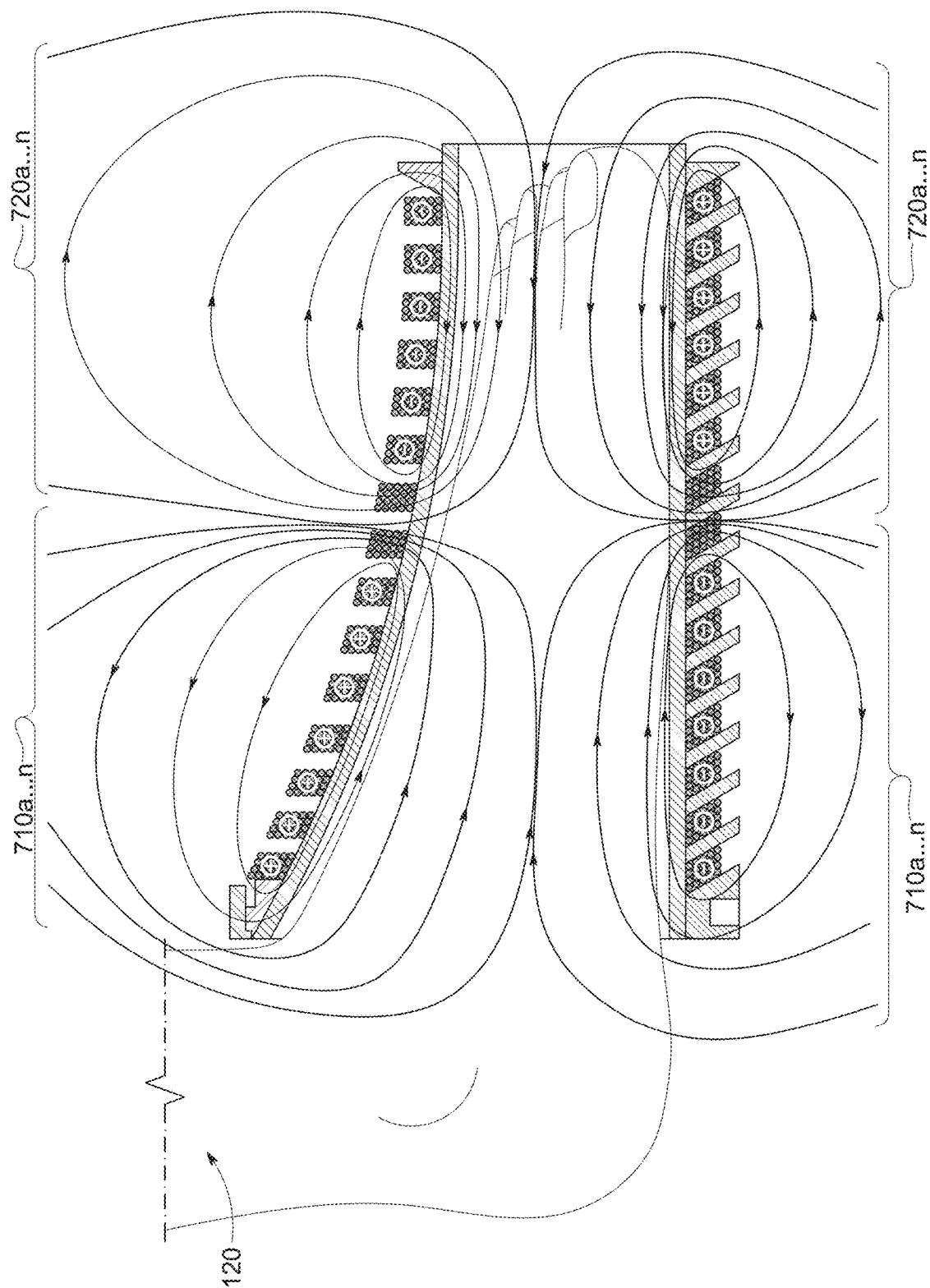
FIG. 7 demonstrates utilizing specific coil groups of alternating polarity (group one consisting of 301-307 and group two consisting of 310-315) to create controlled flux patterns 710a ... n, 720a ... n through and around an appendage 120.

An illustration of oriented flux is FIG. 7 which groups coils 710a . . . n into one polarity and 720a . . . n into the opposite polarity while leaving two coils to form a non-energized gap. This creates flux that is up to perpendicular to the normal longitudinal flux at the point of opposition.

The existence of a flux gap is essential. Without a gap the flux from the magnetic reluctance from the coils would exceed the magnetic reluctance within the core, forcing the opposing flux within the core to cancel each other out, resulting in nullification. With a sufficient gap, the reluctance within the core of each opposing section of the solenoid gives preference to the reluctance of the gap and the flux escapes rather than canceling.

In one exemplary embodiment FIG. 2, the forefoot component 200 comprises fifteen (coil 15 would be from FIG. 3, 315 to FIG. 3, 301—see FIG. 16, Coil 15 for reference) independently controllable coils spanning approximately 150 mm of the forefoot region, enabling flux control in 10 mm segments throughout this therapeutically critical area, where many nerve endings and pain points are concentrated.

In FIG. 6, all coils are wound circumferentially and this means that in a cross sectional view the coil windings on top 610a . . . n would be positive (this is an arbitrary designation) and the coil windings on the bottom would be negative. These polarities can be thought of as indicating the directional flow of current and electrons as opposed to a potential relative to ground. As all coils in 600a . . . n have the same polarity, they all produce flux in the same direction, and as the coils are in sufficiently close proximity and sufficiently similarly formed, the flux from adjacent coils will form together into coherent core flux. All coils in this configuration act as a single solenoid and all of them reinforce each other. This type of segmented solenoid was the primary focus of the original application.

We have full independent control over the polarity of each end of each coil by virtue of the half-bridges 1 through 16 illustrated in FIG. 16. If half-bridge 1 is set to a positive voltage, half bridge 2 is set to a negative voltage (as illustrated in FIG. 16) then Coil 1 will be energized and produce flux. Setting half bridge 3 with positive voltage will energize Coil 2. (It should be mentioned that half-bridge 2 is powering both Coil 1 and Coil 2 because of the half-tap wiring configuration. Also, coil 2 is illustrated as being wound in the opposite direction as coil 1 so that the output flux will have the same polarity. Alternatively, the two leads 502, 504 can be swapped instead of reverse winding every other coil. Every even numbered coil in a half-tap arrangement will be reversed in this way with a half-tap configuration.)

Figure 13:
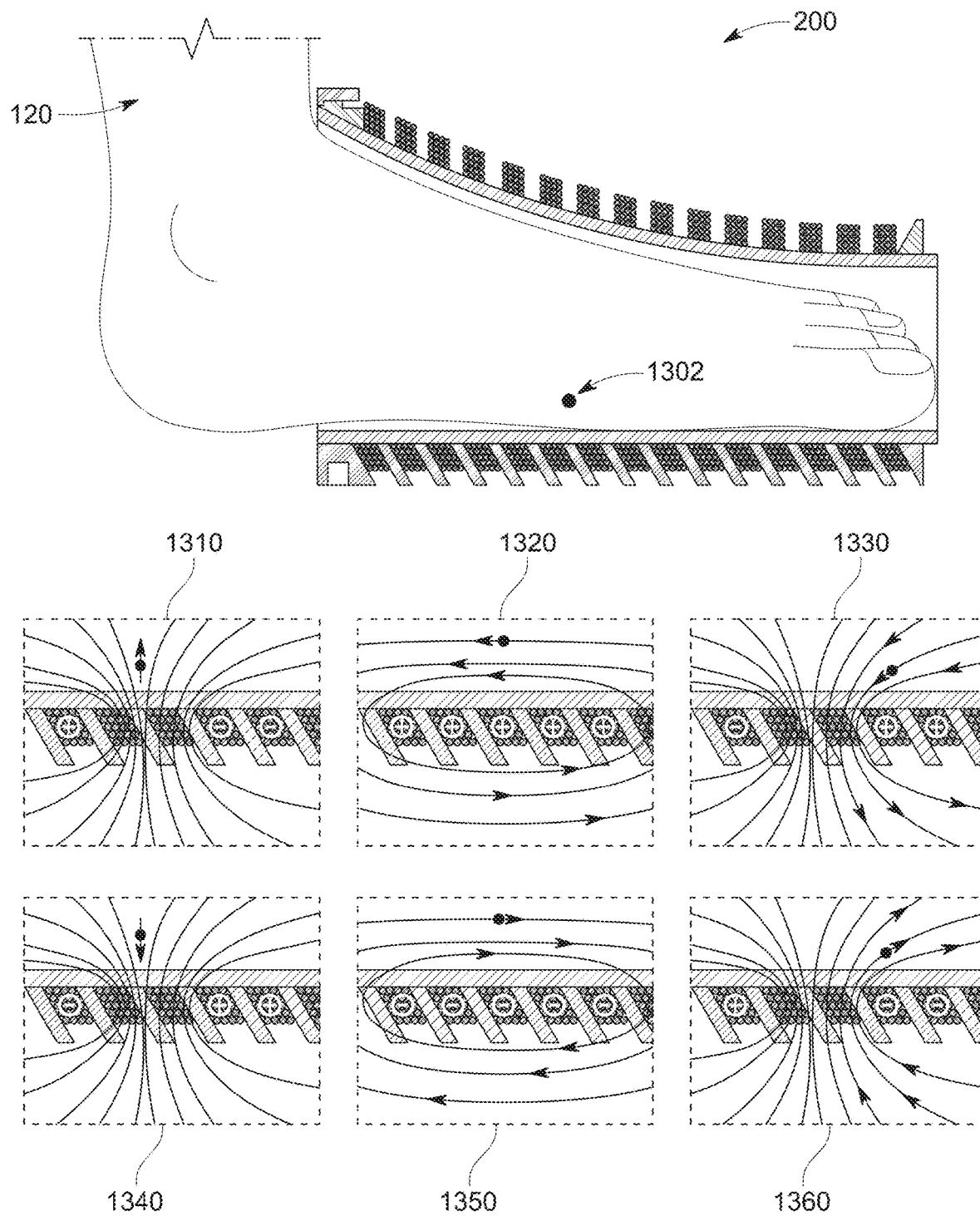
FIG. 13 depicts magnetic flux line relationships to a reference treatment point 1302, showing field patterns for six exemplary activation groups 1310-1360. Reference treatment point 1302 receives flux at an axial orientation of 0° in 1310, at 270° in 1320, at 225° in 1330, at 180° in 1340, at 90° in 1350 and at 45° in 1360. The axial orientation of the flux is indicated by the arrow near the point of reference which is indicated by the dot.
Figure 14A:
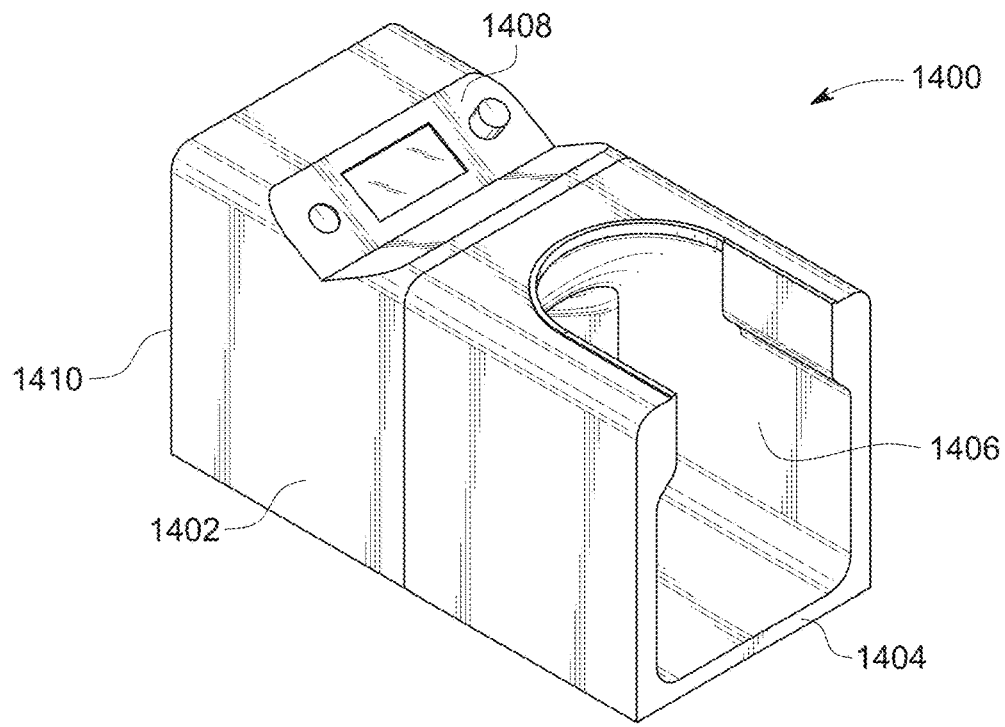
FIG. 14A and FIG. 14B are perspective views showing the housing configuration 1400 with forefoot housing 1402, hindfoot housing 1404, hindfoot opening 1406, display and controller 1408, and forefoot opening 1410.
Figure 14B:
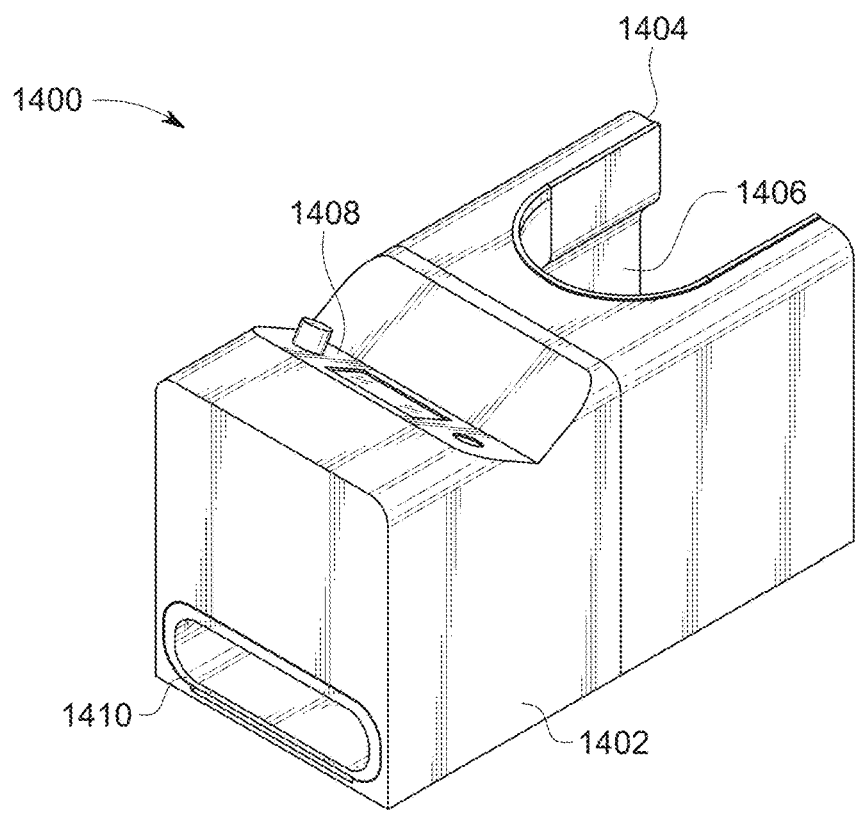

FIG. 7 is a cross-section that illustrates how a solenoid can concurrently produce flux in opposing directions within the same solenoid. Coils 710a . . . n are energized with one polarity ⊕ and coils 720a . . . n are the opposite polarity ⊖. (The ⊕ and ⊖ symbols indicate the current flow and the arrows-indicate the resultant flux direction.) In FIG. 7 two of the coils are not energized and are shown without any ⊕ or ⊖. Within the core of 710a . . . n and also within the core of 720a . . . n the flux is linear, but in directly opposing directions. Where these opposing flux fields meet is called the "point of opposition". Here, they divide as in an island in the middle of a river, and then they re-form into new (somewhat) coherent flux to squeeze through the gap of the two non-energized coils. (What actually happens in the gap is somewhat more complicated because of mutual inductance between the energized and non-energized coils, but it is largely immaterial to the present conceptual description.) What is significant is that the re-formed flux that is escaping through the de-energized coil gap is at 90° to the primary core flux. (The actual angles for most of the flux will be something between 0° and 90°, as illustrated in FIG. 13 illustrations 1310 through 1360.)

What is crucial to this application is that the re-formed flux, resulting from the two opposing core-flux flows, has shifted its orientation by up to 90°. And, importantly, the shifted orientation is greatest near the coils which is also near the surface of the appendage being treated where the nerves are most densely packed. In short: there is a way to cause flux to change orientations within a targeted treatment area.

Figure 8:
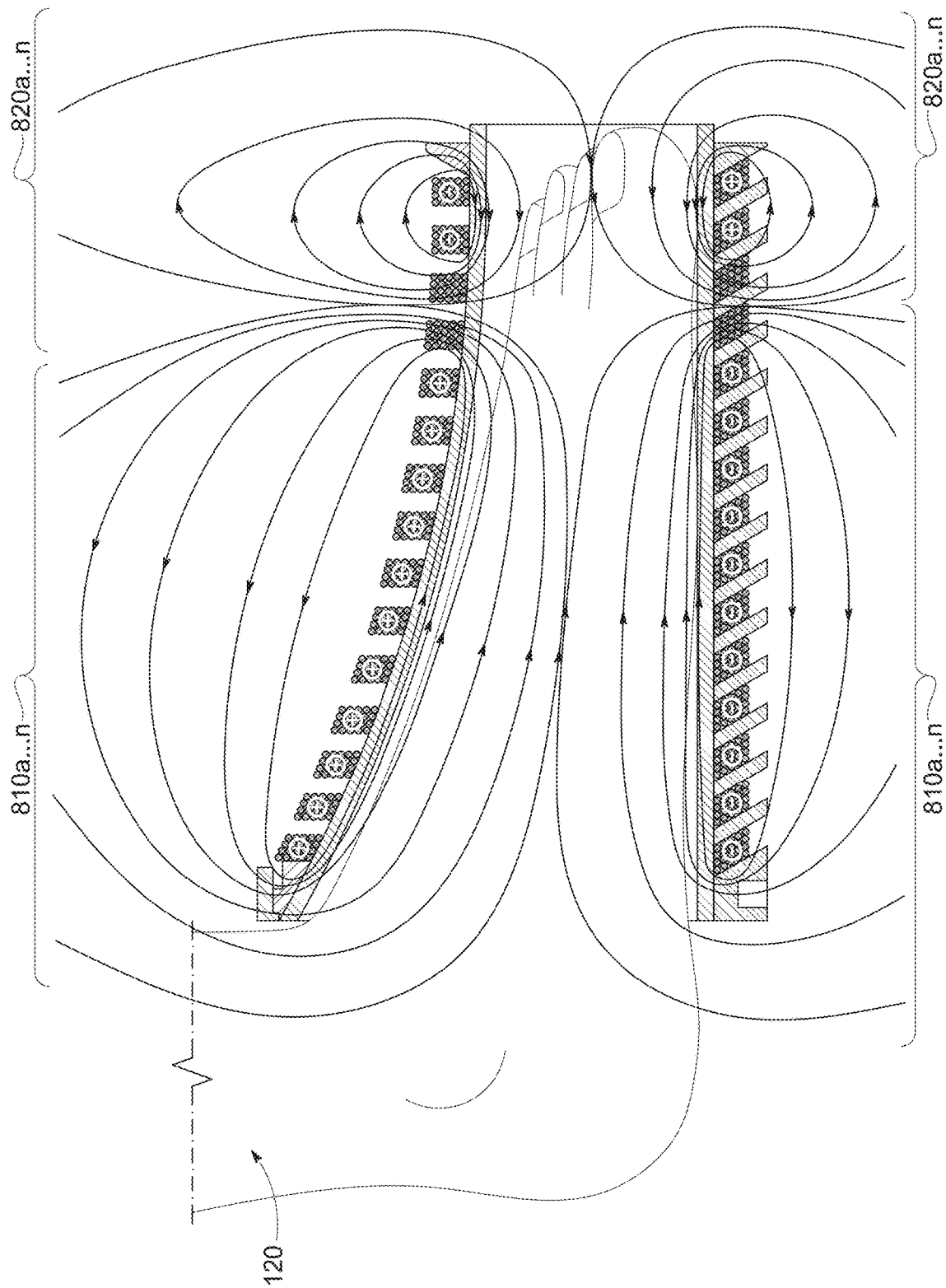
FIG. 8 shows shifting configurations of dynamic flux using coil groups of alternating polarity (group one consisting of 301-311 and group two consisting of 314-315) to generate moving magnetic field patterns 810a ... n and 820a ... n around an appendage 120.
Figure 9:
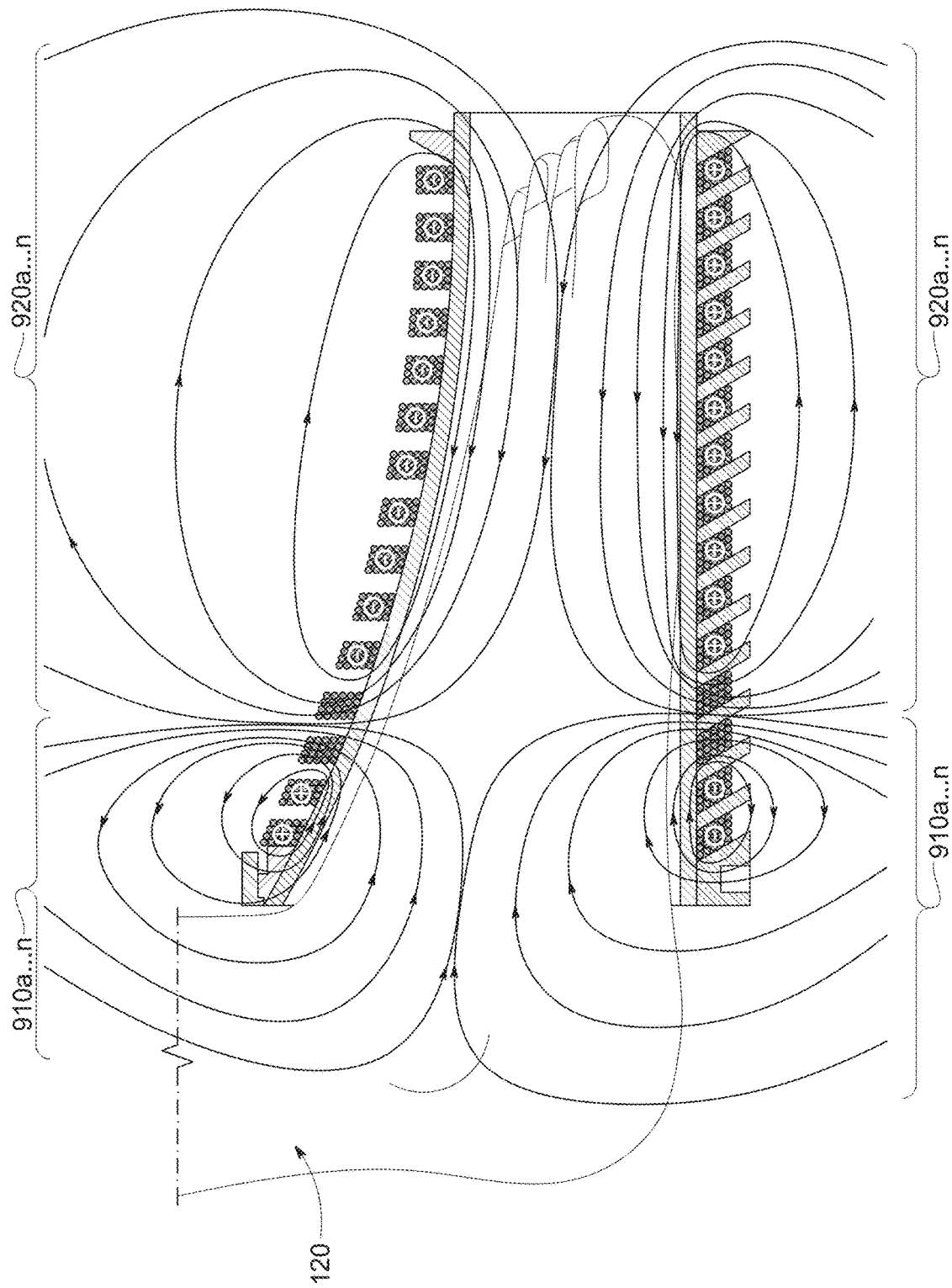
FIG. 9 depicts additional dynamic shifting patterns utilizing coil groups of alternating polarity (group one consisting of 301-302 and group two consisting of 305-315) to create additional complex field interactions 910a ... n and 920a ... n within the treatment zone.

With a segmented solenoid with many segments, the location of the re-oriented flux can be located closely to where it is desired. FIG. 8 illustrates a different location for the point of opposition, as coils 810a . . . n oppose 820a . . . n. These are, of course, the exact same coils, but the configuration of which coils are positive and which are negative is changed, resulting in the re-oriented flux being in a different portion of an inserted foot. FIG. 9 again repositions the point of opposition and the corresponding re-oriented flux through a different combination of coils 910a . . . n and 920a . . . n being configured to produce opposing flux.

Figure 10:
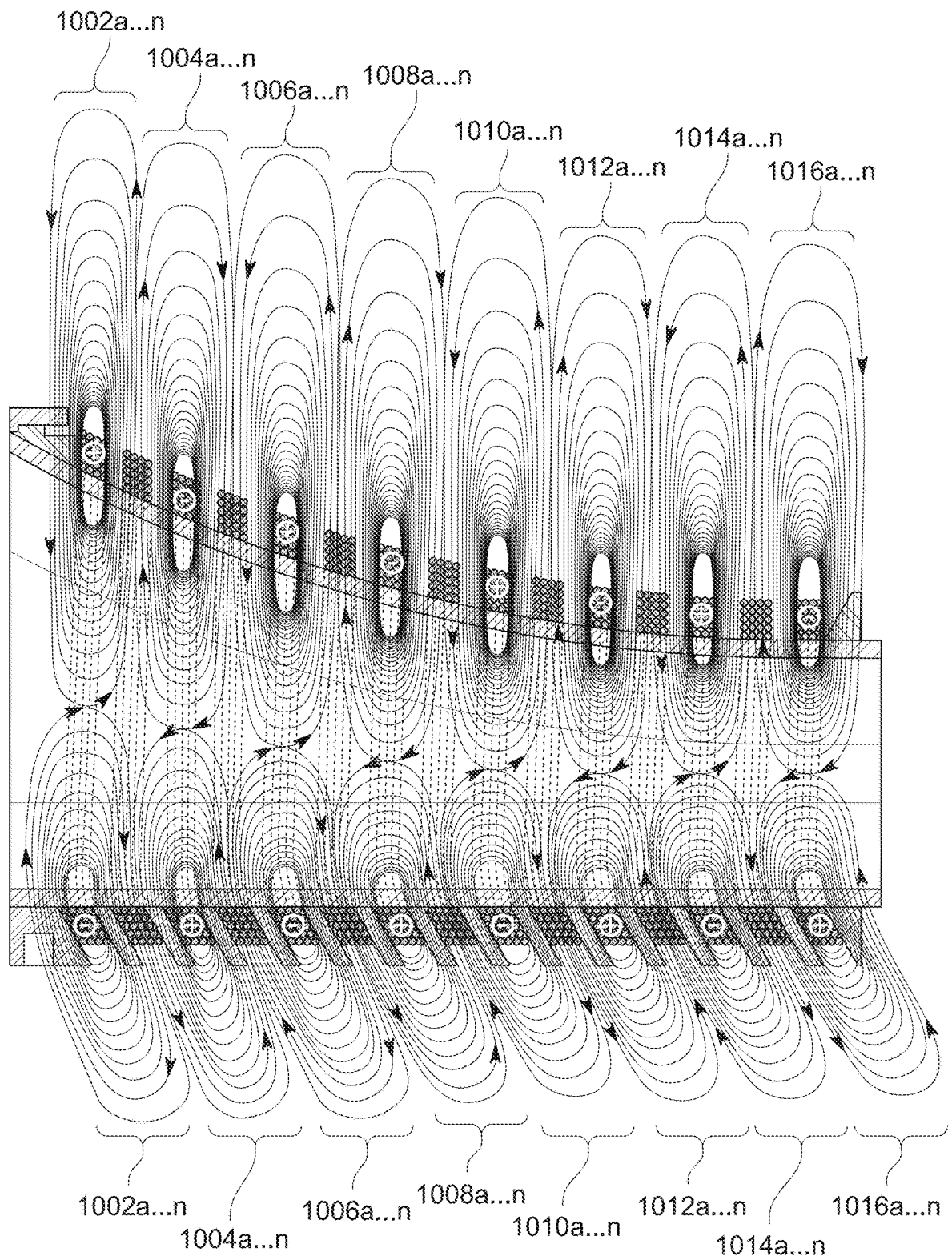
FIG. 10 illustrates near maximum collision point generation through coordinated activation of multiple coil groups of alternating polarity creating controlled flux intersection zones 1002a ... n through 1016a ... n.
Figure 11:
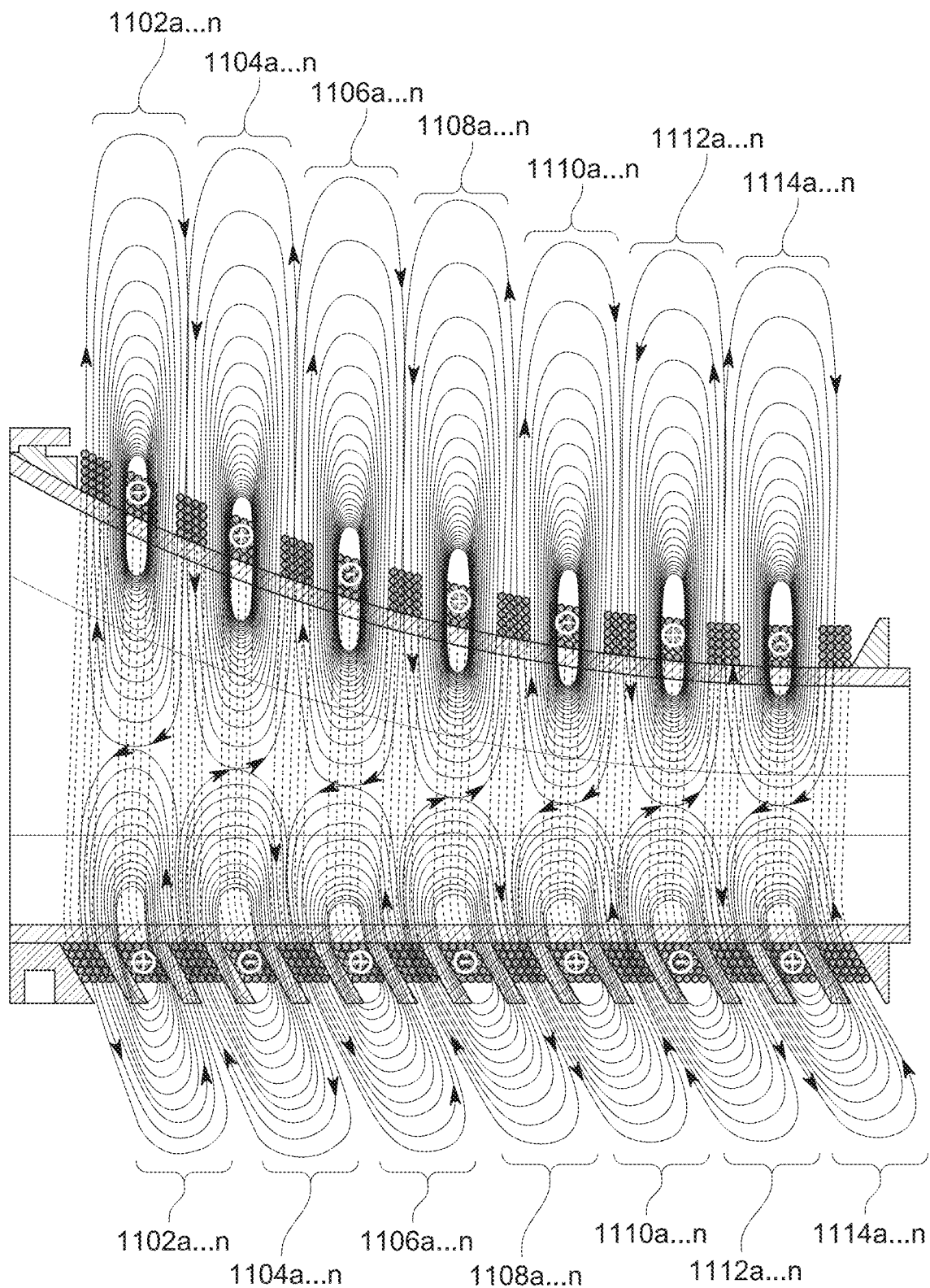
FIG. 11 shows the inverse coil activation pattern 1102a ... n through 1114a ... n from FIG. 10, achieved through selective activation of every other coil group.

FIG. 10 and FIG. 11 taken together illustrate that virtually every part of the treatment area can receive re-oriented flux.

FIG. 10 illustrates every second coil energized and in FIG. 11 the opposite coils are energized. If the flux lines between FIG. 10 and FIG. 11 are compared, it can be seen that every point within the segmented solenoid's treatment area can be coerced into receiving re-oriented flux. The result is that almost all of the flux flows within the treatment target's surface are perpendicular to the segmented solenoid's core. It should be noted that the flux through the non-energized coils can be substantial as its adjacent coils are acting together with flux flows through the gap being in the same orientation.

All of this is accomplished in a straightforward fashion by simply reversing coil polarities using the same electronics package described in the original application. The half bridges FIG. 16 are inherently able to produce current in any polarity, so it is a trivial matter for the polarities to be produced as illustrated in FIG. 10 and FIG. 11.

Taking FIG. 6 to FIG. 12 together, it can be seen that the re-oriented flux is easily created, easily positioned, and easily reversed.

Flux can be re-oriented into an infinite number of angles, not only 90°. FIG. 13 examines an arbitrarily chosen point 1302 to be an example. As illustrated in 1310, 1320, 1330, 1340, 1350, and 1360, this same point (1302) can be subjected to a multitude of flux orientations. By variously configuring which coils are to be non-energized, the angle of flux relative to a point can be altered. The non-energized gap can range from zero coils to many coils. When the gap is larger, the flux lines are more acute and when the gap is smaller the flux lines are more obtuse, relating to the normal longitudinal direction of core flux. FIG. 13 is important because it illustrates that a multitude of flux orientations are possible.

Configuration 1320 demonstrates a substantially orthogonal field pattern relative to 1310, where the reference point 1302 is positioned directly above an activated coil group, resulting in predominantly vertical field lines through the target point. This pattern is achieved by energizing a single coil group beneath the reference point with strong positive polarity while maintaining opposite polarity in adjacent coils, causing field lines to project vertically through the treatment zone.

Configuration 1330 exhibits field patterns similar to 1310 but with the collision zone shifted spatially—while reference point 1302 maintains its absolute position in the treatment volume, it intersects with a different portion of the field pattern due to activation of a different coil group configuration. This shift demonstrates how the same field pattern can be translated through the treatment volume by sequentially activating different coil groups while maintaining their relative polarity relationships. The remaining three configurations 1340, 1350, 1360 mirror their respective counterpart patterns shown in 1310, 1320, 1330 with inverted polarities, demonstrating how each field configuration can be generated with opposite magnetic field orientations through polarity reversal of the contributing coil groups.

Mind the Gap

Reluctance is the hesitancy of flux to pass through a region. It can be thought of as similar to water flowing down a river, if the riverbed were to bend upwards, the water would be reluctant to flow and a lake would form until finally water could flow down again. This happens with magnetic flux, too.

If a segmented solenoid is energized with half the coils on one side being one polarity and half the coils in the opposite polarity, at the point of opposition the reluctance for flux to proceed would be very high. The result is that flux at the point of opposition would try to escape out the sides (similar to two water jets directly facing each other.) Normally, the reluctance close to the coil is greater than at the solenoid's core, forcing the flux in the center to cancel out. When this happens, not much flux flows and the solenoid provides no therapeutic benefit.

The solution is to provide a gap for the flux to escape though the side wall. (Like pulling the opposing water jet nozzles apart slightly.) This is done by having a gap between the opposing solenoid segments. One way to do this is by de-energizing one or more of the segments near the point of opposition, thus providing an escape path for the flux as illustrated in FIG. 6 through FIG. 12.

Zero gap means zero flux, but a small gap means flux with a very high flux density (B) which means that the flux will mostly be at 90° from the point of opposition. As the gap becomes larger the flux density decreases and more and more of the flux will be at angles less than 90°. This can be seen in FIG. 8 where the gap is somewhat wide and the flux angles are everything from 0° to 90° whereas in FIG. 10 and FIG. 11 the gap is narrower and much more of the flux is closer to 90°.

In the preferred embodiment utilizing 15 coils along a treatment zone 150 mm in length, each coil is nominally 10 mm wide. Empirical measurements have demonstrated that the percentage of the core flux escaping through the gap is as follows:

0 mm gap (0 coils): <<10% of core flux escapes.
10 mm gap (1 coil): ≈50% of core flux escapes.
20 mm gap (2 coils): ≈67% of core flux escapes.
30 mm gap (3 coils): ≈75% of core flux escapes.

A gap is optimal at the point of opposition; a narrow (1 coil≈10 mm) gap results in flux escaping perpendicularly at a 90° reorientation; 2 coil or 3 coil gaps result in more flux escaping at a wider variety of angles, which can also be beneficial; gaps of 4 or more coils (with this specific solenoid structure) have diminishing returns.

The preferred embodiment employs de-energized coils to provide the flux gap. But an alternative is to wind the solenoid segments such that there is a gap between the coils comprising the segmented solenoid. Such a solenoid would have a lower overall flux density and probably have fewer segments, but if the gap for a foot-sized solenoid was left at 10 to 15 mm it would be functional. This gap could be between each segment's coil or at chosen points of opposition. Such a configuration eliminates the need to de-energize a coil to allow the flux to escape as there are physical gaps that accomplish this.

Driver Circuitry

FIG. 16 illustrates the fundamental control architecture, centered around the central processing unit 1602. The CPU orchestrates all aspects of system operation through precise control over each coil in the segmented solenoid. In the simplest terms, the CPU 1602 can enable any of the 16 coil drivers shown on FIG. 16 to control any of the 15 coils in the MPTD (each labeled Coil 1 through Coil 15).

An MPTD with 15 coils arranged in a typical multi-tap configuration requires 16 coil drivers. This is because the end drivers only connect to the segmented solenoid's most extreme terminals in a segmented solenoid. If a Coil 16 was added between driver 16 and driver 1 then a loop would be formed, resulting in an undesirable reverse-flow of current. With a multi-tap segmented coil the number of segments will always be less than the number of half-bridge circuits (FIG. 16, FIG. 17).

FIG. 17 shows the circuitry inside each driver 1 through 16 on FIG. 16. This is a typical automotive half bridge with an integrated circuit controller. This type of driver is preferred because the components are readily available, inexpensive, reliable, and have large current handling capabilities. A typical part would be a BTS7960, which provides fast operating times of about 1.6 uS, can connect the output to ground or positive voltage, has adjustable slew rate control, includes thermal protection, voltage protection, and current protection.

The MPTS with DDFC may operate on 24 VDC using an external commercial or medical grade (2×MOOPS) power supply. The voltage could increase to 48 volts (or higher) by using different half-bridge driver circuits. Because concurrent pulsing of 15 coils may have instantaneous peak currents of ≈1,750 amperes, low ESR electrolytic capacitors with total combined capacity of approximately 2,000 µF per coil should be provided on the 24 VDC power rail. This would be 30,000 µF for a 15 coil MPTD. An anti-back-feed SBD diode should be placed between the capacitors and the power supply. The use of a TVS device is recommended close to each coil.

The CPU used in one exemplary configuration is an RP2350 microprocessor embedded into a Pico 2 microcomputer. This contains sufficient RAM, ROM, IO pins, and everything needed for a cost of about five dollars. An RP2350 is an ideal CPU because it has multiple embedded PIO state machines to independently control each GPIO line with 8 nanosecond (or better) resolution, which is 10,000 times faster than an MPTD requires. This excess of speed gives ample headroom to operate the coil drivers with extremely precise timing as well as to drive them in Pulse Width Modulation (PWM) mode in software.

This control architecture enables precise management of magnetic pulses within specific therapeutic parameters. According to various embodiments, the system may generate pulse durations between 50 and 500 uS pulse rates between 1 and 50 pulses per second. Peak current delivery is typically between 500 and 2,500 amperes per pulse, ensuring sufficient field strength for therapeutic efficacy. These operating parameters enable the generation of magnetic fields exceeding 10 mT (and typically in the range of 20 mT to 30 mT) at 10 mm penetration depth, crucial for effective therapeutic stimulation while maintaining safe operation within established electromagnetic exposure guidelines.

Dynamic Direction Flux Control (DDFC)

In a basic MPTD without Dynamic Direction Flux Control (DDFC) a simple strategy may be to configure all of the segmented solenoid's coils that encircle the area to be treated such that they produce flux in one orientation. Then, after half the desired pulse width duration the polarity of all coils is reversed to create a bipolar pulse which brings the cell charge back to zero. This "bipolar pulse sequence" is how the MPTD in the original application operated.

The application of oriented flux to the treatment area is, fortunately, remarkably simple. The entire foot (or portion thereof) can be handled en masse. At least one goal is to treat an entire longitudinal zone and everything within this zone.

The first pulse under DDFC starts the same as does every pulse in the device in the original application, pulsing all coils on, reversing polarity, and then off in the standard bipolar pulse sequence. (Symbolized by ⊕ since the first part of the bipolar pulse is positive.)

For the next 15 pulses, a non-energized gap is shifted through each of the 15 segments of the solenoid as follows:

1) The end-most coil (Coil 1, 301) is configured to not energize ⊗. All other coil positions (Coil 2, 302 through Coil 15, 315) are set to positive-leading ⊕ pulses and then a bipolar pulse sequence is performed.
2) The configuration of non-energized coil ⊗ is shifted from the end 301 so that the non-energized coil will be the next be position 302 and its former position 301 is now configured for a negative bipolar pulse sequence. Thus, coil 301 opposes that of the rest of the coils (303 . . . 315) creating a point of opposition ⊗ at coil 302. Another bipolar pulse sequence is performed. Note that the pulse produced by coil 301 is bipolar, but it starts with a negative polarity and in the middle is made positive while coils 303 . . . 315 start with a positive polarity and in the middle they are made negative. (The ⊖ and ⊕ symbols therefore represent the polarity of the first half of bipolar signals.)
3) The previous step is repeated for each remaining pulse, with the non-energized coil configuration sequencing each pulse from 301 to 302 to 303 until finally reaching 315. As formerly non-energized ⊗ coils are re-enabled they are set to the opposing polarity ⊖ that matches 301.

Figure 18:
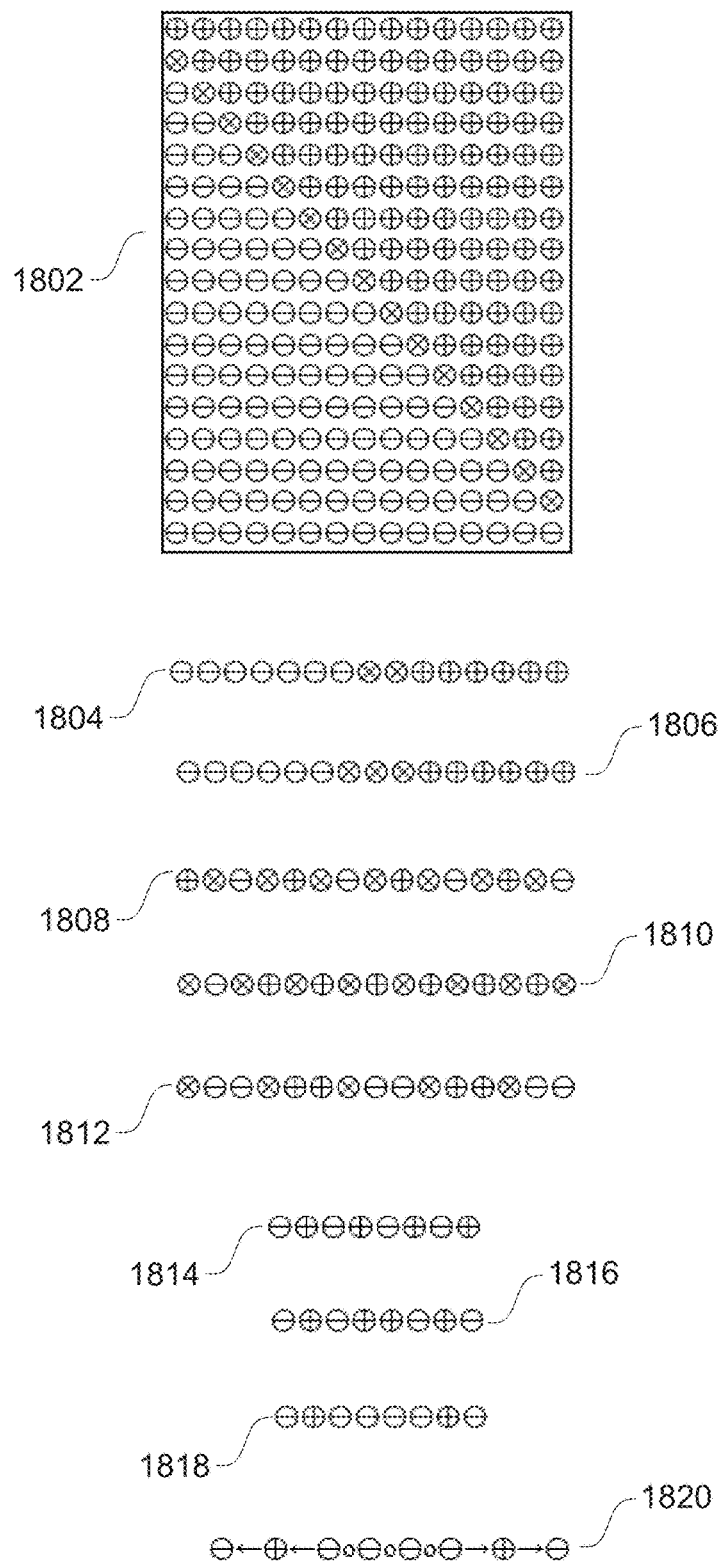
FIG. 18 shows symbolic representations of at least some coil configurations wherein the ⊕ and ⊖ symbols indicate the current flow, the ⊗ symbol is a coil that is not energized, and the arrows ← → indicate the resultant flux direction.

The table 1802 on FIG. 18 visually illustrates the above steps shifting the gap through the coils of the segmented solenoid so that every segment receives re-oriented flux. Each line represents one concurrent pulse of all of the coils in the segmented solenoid. The symbol ⊕ represents a coil whose bipolar pulse sequence has an initial positive polarity, the symbol ⊖ represents a coil whose bipolar pulse sequence has an initial negative polarity, and the symbol ⊗ represents a coil that is not energized.

1802, FIG. 18 illustrates a sequence of 17 total pulses, with the first being all coils with their initial bipolar pulse sequence positive ⊕ and the last pulse being with all coils with their initial bipolar pulse sequence being negative ⊖

A good way to visualize this is as shift-register-like sequencing that continues until the entire solenoid is the opposite polarity for the initial portion of the bipolar pulses from when the sequence started. The non-energized coil configuration "shifts" from 301 to 315. The coils with lower numbers are one polarity and the coils with higher numbers are the opposing phase. The first and last pulses have all coils enabled. A total of 17 pulses forms the complete sequence.

Visually, it would be like chaser lights on a Las Vegas sign. Using the Las Vegas sign analogy is useful and accurate. It immediately brings to mind that a wide variety of chaser-light patterns are possible, and this correctly implies that any number of DDFC pulse sequence patterns are also possible. It isn't necessary to sequentially sequence from lowest 301 to highest 315 numbered coil.

Perhaps two adjacent non-energized positions travel through the pattern shown in 1804, FIG. 18.

Perhaps three adjacent non-energized positions travel through the pattern 1806, FIG. 18.

Figure 12:
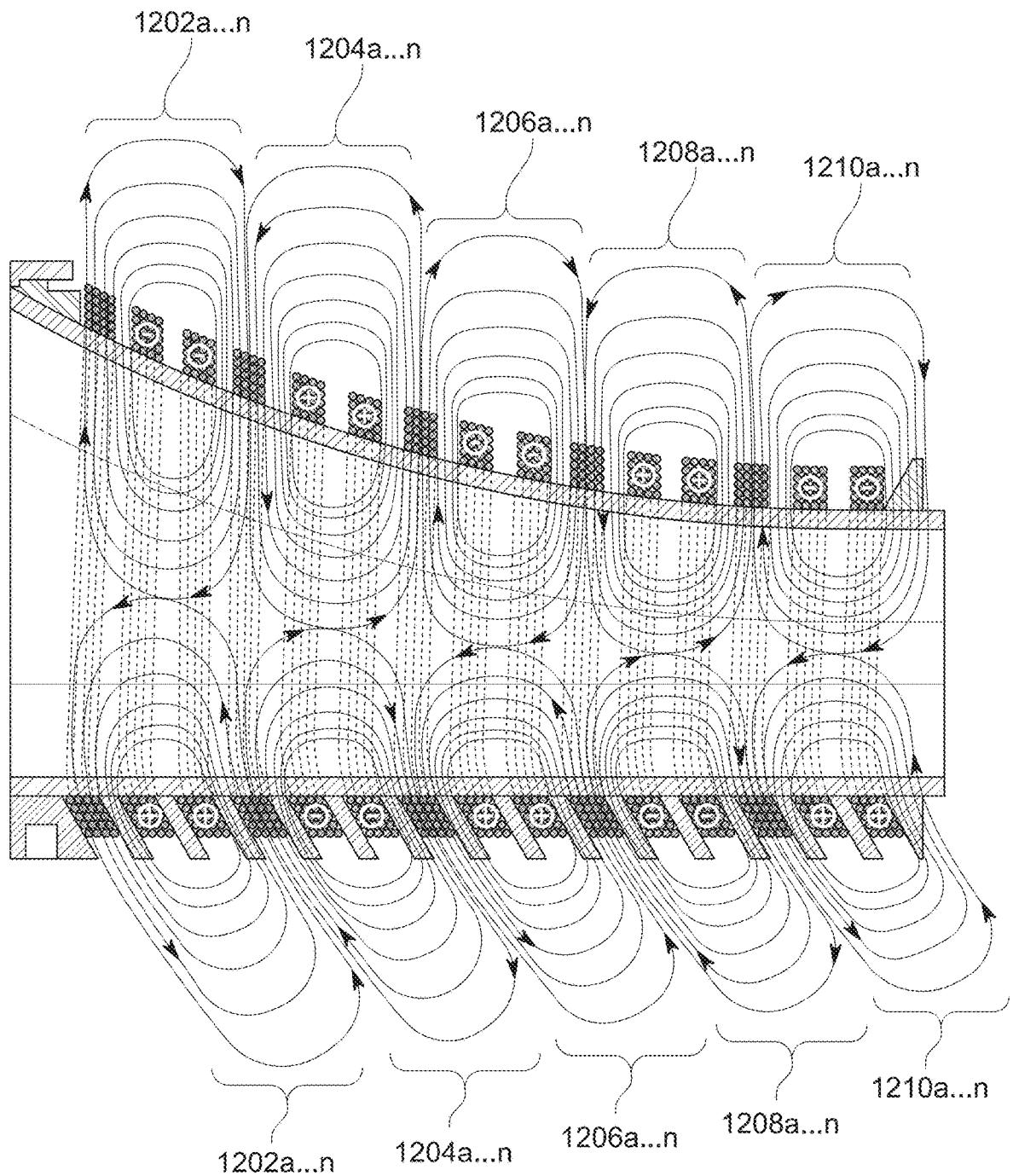
FIG. 12 demonstrates further collision point configurations 1202a ... n through 1210a ... n using coil groups for specialized therapeutic patterns.

Perhaps corresponding alternating patterns are FIG. 10 corresponding with FIG. 18, 1808, FIG. 11 corresponding with FIG. 18, 1810, and FIG. 12 corresponding with FIG. 18, 1812.

There is a limitless number of sequences, patterns, chase effects, gaps, and pulse durations, all of which serve the purpose of exposing a treatment target to magnetic flux of varying orientations. Any of these infinite possibilities of patterns use the basic principle of the present invention: vary the orientation of the flux within the treatment target so as to maximize cellular reception of the magnetic pulses. The underlying principle always remains: use the coils in a segmented solenoid to create gaps and opposing flux polarities so as to re-orient flux in non-longitudinal ways.

Looking again at the study point 1302 on FIG. 13 it can be seen that any of the orientations 1310 through 1360 will be obtained at nearly every point within the treatment zone through sequencing through each of the coils and using one, two, or three coil gaps.

DDFC Combined with Multi-Tap Coils

In a conventional segmented solenoid one wire from each segment coil might be connected to High-Side (V-Coil) voltage, usually from a capacitor. The other leg of each segment is connected to a low-side MOSFET. The coil can be individually switched on and off from a logic source. This yields a unipolar magnetic pulse.

To produce a bipolar magnetic pulse using conventional wiring each side of each segment coil is connected to a half-bridge, the resultant circuit being a full-bridge. This allows the coil to be energized in either polarity which provides bipolar pulses and each phase can therefore be double the swing (+ΔB to −ΔB). However, this requires twice the GPIO lines and twice the drivers with four times the MOSFETs.

The original application introduced the use of multi-tap coils in a segmented solenoid used as an MPTD. This provided for bipolar pulses with half as many control lines, and half as many drivers. A multi-tap configuration generally requires that every other coil be wound in reverse, or that the coil lines be swapped. The driver circuit for multitap shares a half bridge between two (typically adjacent) coils and therefore without the winding or lead reversal adjacent coils will cancel each other out. This was all discussed in some detail in the original application.

Dynamic Direction Flux Control (DDFC) is compatible with a multi-tap wiring configuration, although it may not be apparent how to implement it given that a gap is important and multi-tap offers no readily apparent way to not power a specific coil. Execution is, thankfully, straightforward.

Consider a traditional driver configuration to produce a pulse in a segmented solenoid. To power a coil, the adjacent half bridges should be configured with opposite polarities. The half bridges would therefore be configured as shown in FIG. 18, 1814 (this represents 8 drivers and 7 coils in a multi-tap configuration. Flux would travel from one axial end of the solenoid to the opposite axial end.

A point of opposition would be created with this configuration corresponding shown in FIG. 18, 1816. The point of opposition would be in the middle of the solenoid where the fourth coil connects to the half bridges configured as ⊕⊕. Since both ends of coil four have the same polarity, the fourth coil is unenergized. (The same would be true of the drivers for a coil were ⊖⊖. As long as the polarity of the adjacent drivers is the same the coil between them will be unpowered.) It is noteworthy that FIG. 18, 1816 creates a point of opposition and also it creates a single coil gap at the point of opposition because the driver configuration ⊕⊕ results in one coil being unpowered.

Frequently a multi-coil gap is desirable, and this is easily accomplished in a multi-tap configuration. FIG. 18, 1818 shows a driver configuration which results in a three-coil gap. FIG. 18, 1820 is the same configuration with arrows indicating the flux direction, taking into account the coil winding reversal.

These rules need to be considered when configuring drivers in a multi-tap configuration:

1) Every other coil is wound or wired in reverse, and therefore the drivers for that coil must be reversed from the adjacent coil to maintain the same flux orientation.
2) Adjacent drivers being the same output polarity will always create a one coil gap.
3) Gaps must be an odd number of coils in a true multi-tap configuration. A two or four coil gap where there is a point of opposition cannot exist in a multitap configuration (but of course can exist with conventional non-multitap wiring.)
4) Gaps consisting of an even number of coils in a multi-tap configuration can be created, not with a point of opposition. An even-number or coil gap will leak or eject non-opposition flux and can be used for DDFC, but the leaking flux will be lower quality. (See discussion on Non-opposition oriented flux, below as it is also applicable to even numbered gaps in a multi-tap configuration.)

It practice, multi-tap works well with DDFC and it is easy to implement, and one or three coil gaps are generally ideal in their flux ejection characteristics.

Treatment Protocols

A "treatment protocol" is typically a set of instructions, parameters, or steps that specifies the timing, duration, sequencing, power, waveform, coil selection and coil polarities for a treatment session. The treatment protocol can provide separate parameters for zones within the segmented solenoid. Emphasis can be given to the toes by intensifying the pulses for coils 310 through 315. Over-stimulation of the inner arch can be prevented by de-emphasizing coils 301 through 305. This provides an immense degree of targeting since each area throughout the segmented solenoid can be specifically treated.

These treatment protocols may be pre-programmed by the factory and stored locally within the device, created and sent to the device by providers bespoke for each patient, created by users through the device display, an app or a web interface, or any other means of software distribution. Treatment protocols can be sent to the device over the Internet, via removable media, communication cables, Bluetooth, or other ways. If the device has a control panel, it can be configured to allow a user to choose from a selection of treatment protocols. Or, treatment protocols may be able to be modified through the control panel or an app to modify a treatment protocol's session duration, treatment area zones, intensity or objectives.

Use of Pulse Width Modulation

An electronic circuit where individual coil power is varied would offer control over flux orientation. Rather than non-powering coils within the segmented solenoid to create a gap, coil power may be modulated. Just as non-powering a coil within a segmented solenoid reduces reluctance along the perimeter of the solenoid's core, allowing core flux to escape, the same can be accomplished by reducing power to some coils.

Consider three contiguous coils used to form a gap in the segmented solenoid where the center coil is non-energized and the two adjacent coils are energized with lower power levels. This would form a gap at the point of opposition that was less defined and that had "softer edges". The result would be more flux escaping at more acute angles.

Similarly, the two adjacent coils can be actively modulated throughout the bipolar pulse sequence. Because magnetic flux re-forms at close to the speed of light, rapid modulation of the adjacent coils would be much like an oscillating lawn sprinkler forcing water to disperse in all directions.

There are several ways of controlling the power level in coils. There are many well understood ways of controlling the power level to a specific coil, but the most preferred approach is through the use of Pulse Width Modulation (PWM). The RP2350 can perform PWM on any GPIO line in hardware, so setting up a PWM at a high frequency with a particular duty cycle is simply a matter of setting parameters. (Of course, the RP2350 is fast enough that it could be done in software, too.) It is recommended to use a low-pass filter capacitor to integrate the voltage when using PWM. This needs to be a very high-speed device; it has been found that polypropylene or polyester capacitors work well at values of between 10 to 100 µF.

The present circuit shown in FIG. 17 (which is the same as FIG. 13 in the original application) is fully capable of controlling coil power through Pulse Width Modulation (PWM) at reasonable frequencies (about 250 khz). This means that gap coils can be easily PWM modulated using the MPTD hardware disclosed in the original application, resulting in the "spraying" of oriented flux escaping through the gap at a multitude of angles.

Non-Opposition Oriented Flux

A segmented solenoid can generate non-opposition-oriented flux-magnetic flux that is neither axially aligned nor arises from opposing coil fields. This flux is characterized by low intensity, poor coherence, and limited directional control, produced when only a subset of the solenoid's coils is energized rather than paired in opposition.

For instance, in FIG. 7, energizing coils 720$a$ ... $n$ while leaving coils 710$a$ ... $n$ unpowered causes flux lines from 720$a$ ... $n$ to pass through 710$a$ ... $n$ at a non-axial angle—roughly diagonal and misaligned with the solenoid's core. These lines are weak, scattered, and lack uniformity. Similarly, in FIG. 10, if coils 1006$a$ ... $n$ and 1010$a$ ... $n$ are energized but 1008$a$ ... $n$ are not, flux near 1008$a$ ... $n$ becomes highly irregular, with inconsistent direction and even lower coherence due to the wider unpowered gap.

All non-opposition flux shares this low-grade, non-coherent, low-intensity profile. It technically qualifies as "oriented flux" due to some directional bias, but its therapeutic value is minimal. Intentionally sequencing coil energization—such as activating different subsets or individual coils in a pattern without opposition—can produce varied flux orientations across the treatment zone. While this counts as "dynamically oriented flux," it lacks the precision and strength of opposition-driven flux and is not the invention's primary objective.

This non-opposition flux differs fundamentally from end-axis flux, a byproduct of all open-ended solenoids. End-axis flux emerges where the solenoid's core flux exits one end, loops externally around the device, and returns to the opposite end to complete the magnetic circuit. This flux is inherently oriented (following the loop path), but it occurs outside the treatment zone—at the solenoid's axial extremities—making it incidental and therapeutically irrelevant within the core. Its intensity diminishes rapidly with distance from the ends, rendering it a low-quality field.

In a segmented solenoid, energizing select coils—for example, a distal subset to treat the toes-produces incidental non-opposition flux through adjacent unpowered coils, extending beyond the target area. This flux, while oriented, is an unintended side effect, not designed for therapy in those regions. Contrast this with intentional sequencing: energizing coils one-by-one from end to end maintains a common flux direction, deliberately generating low-grade non-opposition flux throughout the treatment zone. The distinction lies in purpose and scope: end-axis flux is an unavoidable, external loop beyond the energized portion of the core, whereas intentionally sequenced non-opposition flux aims to permeate the treatment zone, albeit with limited therapeutic efficacy due to its weak, scattered nature.

Alternative Embodiments

In alternative embodiments, the device may comprise many independently controllable coils spanning the entire length of the foot, from toe to heel. This is illustrated in FIG. 4 And also in the original application in FIG. 1 at 13 and FIG. 6B at 69. For example, if using an average foot length of 250 mm, a reasonable number of coils may be twenty-three (23) independently controllable coils spanning the entire length of the foot, from toe to heel. This full-foot configuration maintains the same precise segment control while extending treatment coverage to include the mid-foot, arch, and heel regions. The additional coils enable sophisticated flux pattern control throughout the entire foot.

Figure 15A:
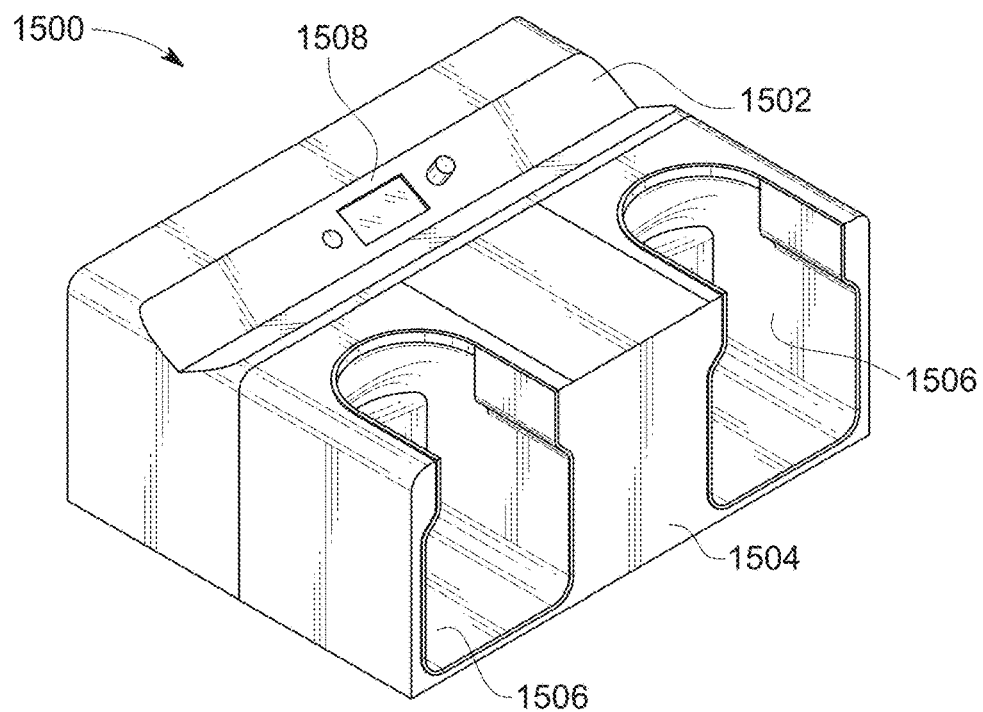
FIG. 15A and FIG. 15B illustrate a dual foot housing configuration 1500 featuring forefoot housing 1502, hindfoot housing 1504, hindfoot openings 1506, and display and controller 1508.
Figure 15B:
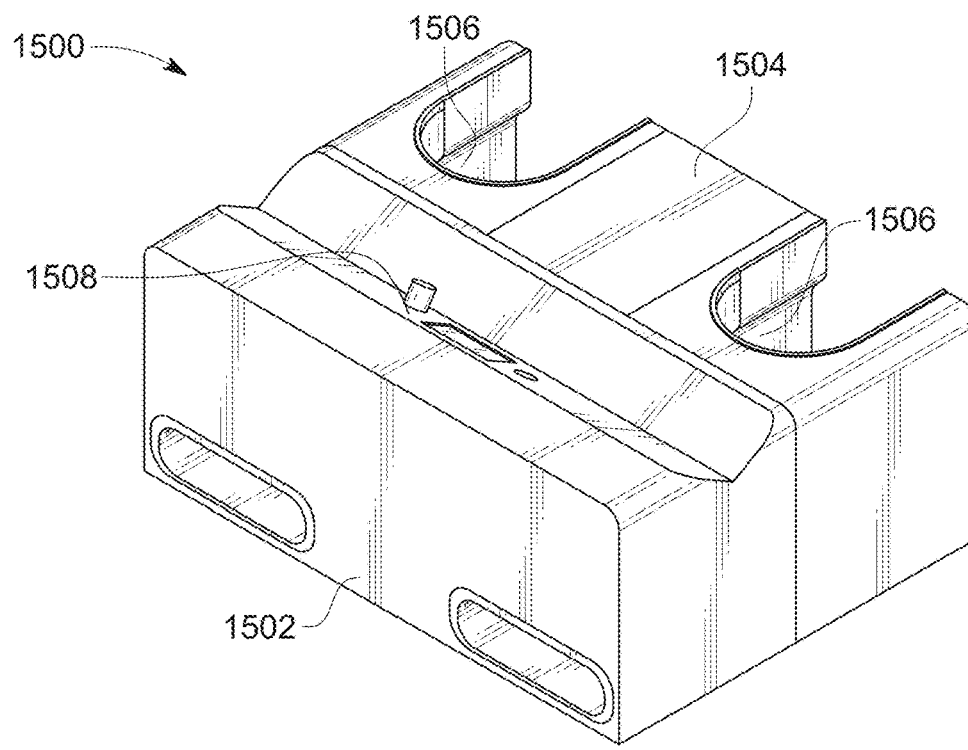

FIG. 15A and FIG. 15B present a dual-foot configuration 1500 that enables simultaneous treatment of two appendages. This integrated design incorporates separate forefoot housings 1502 and hindfoot housings 1504 while maintaining independent control over each treatment zone. Multiple hindfoot openings 1506 facilitate seamless positioning of both appendages, while a centralized display and controller interface 1508 enables coordinated management of both treatment zones through a single control point.

It will be appreciated by those skilled in the art that the number and arrangement of coils, patterns of activation, and shape and style of the housing described in the exemplary embodiments serve illustrative purposes and should not be construed as limiting. The principles and methods of dynamic directional flux control (DDFC) disclosed herein may be implemented in various configurations, with different quantities of coils arranged around different applicators of different dimensions, all adapted to accommodate appendages of varying sizes and therapeutic requirements. The fundamental concepts of dynamic directional flux control (DDFC) which employ independent coil control and dynamic flux manipulation of a segmented solenoid remain applicable across these various implementations, enabling the creation of sophisticated magnetic field patterns regardless of the specific physical configuration chosen.

SUMMARY

Dynamic Directional Flux Control (DDFC) provides the ability to re-orient flux within a treatment zone created by a segmented solenoid. A wide variety of flux orientations are possible, and the position of these flux reorientations can be precisely positioned throughout the segmented solenoid. An MPTD with DDFC can offer the full range of flux orientations that a skillful technician can perform, and it can do it in a precise, repeatable, controlled way that a human operating a manual applicator cannot do.

The use of a DDFC device stimulates cellular structures and nerve pathways more effectively than traditional single-orientation systems.

This oriented flux method works in practice. It has been built and measured in a laboratory, and it performs well. The re-oriented flux is strong, the all-important dB/dt is typically high, often in the range of 80 Tesla/second or more, and the re-oriented flux density is well above conventionally understood therapeutically levels. Intensive use of oriented flux does not generate measurably more heat, it does not increase capacitor stress, it poses no known safety concern, and it does not increase device manufacturing cost.

Implementing oriented flux capabilities in an MPTD as disclosed in the original application can be done at no hardware cost whatsoever. The electronics proposed in the present application are, to practical effect, no different than the electronics proposed in the original application.

An MPTD equipped with DDFC provides superior magnetic pulse therapy. It is simple, safe, effective, and both easy and inexpensive to implement.

In closing, the inventor has invented and reduced to practice a magnetic pulse therapy device comprising: a segmented solenoid comprising a plurality of independently controllable coils arranged to form a treatment zone within its core; a controller configured to: energize a first subset of the coils to produce magnetic flux in a first direction; and energize a second subset of the coils to produce magnetic flux in a second direction opposing the first direction, thereby creating a point of opposition between the first and second subsets; and a gap near the point of opposition that allows magnetic flux to escape laterally from the solenoid.

Aspects of the invention are: a) an applicator defining a cavity configured to receive a human appendage, wherein the segmented solenoid is disposed within or around the applicator surrounding the cavity; b) wherein the cavity is shaped to receive a human foot and the applicator includes a proximal opening allowing insertion and removal of the human foot without manual grasping or assistance; c) wherein the controller is configured to vary the location of the point of opposition and the gap during a treatment session by selectively energizing different subsets of coils; d) wherein the controller is configured to vary the location or presence of the point of opposition and the gap throughout a pulse by selectively energizing different subsets of coils, during which at least one coil remains energized as the configuration of energized coils changes one or more times; e) wherein the controller is configured to execute a treatment protocol, and the treatment protocol is selected by one or more of: (a) the user choosing from a selection of pre-programmed treatment protocols, (b) the user modifying protocol parameters through a control panel or an app to modify a treatment protocol's session duration, treatment area zones, intensity or objectives, and (c) a provider selecting the treatment protocol; f) wherein subsets of coils may have different treatment protocols; g) wherein at least some of the coils are configured in a multi-tap configuration; h) wherein the controller is configured to energize the coils with a nominal voltage of 50V DC or less; i) wherein the controller is capable of energizing the coils with a cumulative peak current exceeding 250 amperes; and j) wherein the controller is configured to supply power to the coils using pulse width modulation, thereby modulating the strength of the magnetic flux.

The inventor has also reduced to practice a method for magnetic pulse therapy comprising: providing a segmented solenoid comprising a plurality of independently controllable coils forming a treatment zone within its air core; controlling a first subset of the coils to produce magnetic flux directed in a first direction; controlling a second subset of the coils to produce magnetic flux directed in an opposing direction, thereby creating a point of opposition between the first and second subsets; and forming a gap near the point of opposition allowing magnetic flux to escape laterally from the solenoid's side wall.

Aspects of the said method may be: a) varying the location of the point of opposition and the gap during a treatment session by selectively energizing or non-energizing different subsets of coils; b) varying the location or presence of the point of opposition and the gap throughout a pulse by selectively energizing or non-energizing different subsets of coils while ensuring at least one coil remains energized as the configuration of energized coils changes one or more times; c) providing the treatment zone shaped to receive a human foot with a proximal opening and inserting the human foot into the treatment zone through the proximal opening without manual grasping or assistance; and d) wherein the coils are configured in a multi-tap configuration.

The inventor has reduced to practice a magnetic pulse therapy device for specifically treating a human foot, comprising: an applicator having a cavity shaped to receive at least a portion of a human foot, accessible through a proximal opening; a segmented solenoid comprising a plurality of independently controllable coils arranged circumferentially around and longitudinally along the cavity; and a controller configured to selectively control the coils to produce opposing magnetic flux directions with one or more points of opposition and gaps between them, thereby dynamically directing magnetic flux within the cavity to target specific areas of the foot.

Aspects of the MPTD for foot treatment may include: a) wherein the controller is configured to: control a first subset of the coils to produce magnetic flux directed in a first direction; control a second subset of the coils to produce magnetic flux directed in an opposing direction; and form a gap by non-energizing one or more coils between the first and second subsets, thereby directing magnetic flux within the cavity to target specific areas of the foot, b) wherein the controller is configured to vary the location of the point of opposition and the gap during a treatment session by selectively energizing or non-energizing different subsets of coils: (a) between pulses; or (b) throughout a pulse, during which at least one coil remains energized as the configuration of energized or non-energized coils changes one or more times; c) wherein the controller is configured to execute a treatment protocol, and the treatment protocol is selected by one or more of: (a) the user choosing from a selection of pre-programmed treatment protocols; (b) the user modifying protocol parameters through a control panel or an app to modify a treatment protocol's session duration, treatment area zones, intensity, or objectives; and (c) a provider selecting the treatment protocol; d) wherein subsets of coils may have different treatment protocols; e) wherein at least some of the coils are configured in a multi-tap configuration; and f) wherein the proximal opening is configured to allow insertion and removal of the human foot by sliding the human foot laterally into the cavity without navigating around obstructions.

The inventor has also reduced to practice a magnetic therapy device comprising: a segmented solenoid having multiple coils; wherein the coils are configured to produce magnetic flux that escapes laterally from the solenoid for therapeutic effect within a treatment zone defined as the longitudinal length from the furthest most energized coils in a treatment session, the magnetic flux including at least one of the following techniques: (a) opposing flux produced by energizing a first subset of the coils to generate flux in a first direction and a second subset of the coils to generate flux in an opposing direction; or (b) non-opposing flux produced by energizing a subset of the coils for the purpose of creating therapeutic flux within the treatment zone while adjacent coils remain non-energized, distinct from unintentional end-axis flux occurring outside the treatment zone.

Aspects of said device may include: a) wherein the coils are configured to vary the location of the point of opposition and the gap during a treatment session by selectively energizing or non-energizing different subsets of the coils: (a) between pulses; or (b) throughout a pulse, during which at least one coil remains energized as the configuration of energized coils changes one or more times; b) wherein the coils are configured to enable dynamic variation of the region by selectively periodically energizing different coil subsets, thereby adjusting the location or presence of one or more opposition points and associated flux escape zones during operation to optimize therapeutic targeting across the treatment zone; c) wherein subsets of coils may have different treatment protocols; and d) wherein at least some of the coils are configured in a multi-tap configuration.

What is claimed is:

1. A magnetic pulse therapy device comprising:
    a segmented solenoid comprising a plurality of independently controllable coils arranged to form a treatment zone within its core;
    a controller configured to:
        energize a first subset of the coils to produce magnetic flux in a first direction; and
        energize a second subset of the coils to produce magnetic flux in a second direction opposing the first direction, thereby creating a point of opposition between the first and second subsets; and
    a gap near the point of opposition that allows magnetic flux to escape laterally from the solenoid.

2. The device of claim 1, further comprising an applicator defining a cavity configured to receive a human appendage, wherein the segmented solenoid is disposed within or around the applicator surrounding the cavity.

3. The device of claim 2, wherein the cavity is shaped to receive a human foot and the applicator includes a proximal opening allowing insertion and removal of the human foot without manual grasping or assistance.

4. The device of claim 2, wherein the controller is configured to vary a location or presence of the point of opposition and the gap by selectively energizing different subsets of the independently controllable coils either (a) throughout a pulse, or (b) throughout a treatment session, or both such that at least one of the independently controllable coils remains energized as the configuration of energized coils changes one or more times.

5. The device of claim 1, wherein the controller is configured to vary a location of the point of opposition and the gap during a treatment session by selectively energizing different subsets of coils.

6. The device of claim 1, wherein the controller is configured to execute a treatment protocol, and the treatment protocol is selected by one or more of:
    (a) a user choosing from a selection of pre-programmed treatment protocols,
    (b) the user modifying protocol parameters through a control panel or an app to modify a treatment protocol's session duration, treatment area zones, intensity or objectives, and
    (c) a provider selecting the treatment protocol.

7. The device of claim 1, wherein subsets of coils belonging to the plurality of independently controllable coils may have different treatment protocols.

8. The device of claim 1, wherein at least some of the coils are configured in a multi-tap configuration.

9. The device of claim 1, wherein the controller is configured to energize the coils with a nominal voltage of 50V DC or less.

10. The device of claim 1, wherein the controller is capable of energizing the coils with a cumulative peak current exceeding 250 amperes.

11. The device of claim 1, wherein the controller is configured to supply power to the coils using pulse width modulation, thereby modulating the strength of the magnetic flux.

12. A method for magnetic pulse therapy comprising:
    providing a segmented solenoid comprising a plurality of independently controllable coils forming a treatment zone within its air core;
    controlling a first subset of the coils to produce magnetic flux directed in a first direction;
    controlling a second subset of the coils to produce magnetic flux directed in an opposing direction, thereby creating a point of opposition between the first and second subsets; and
    forming a gap near the point of opposition allowing magnetic flux to escape laterally from the solenoid's side wall.

13. The method of claim 12, further comprising varying either the point of opposition, the gap, or both during a treatment session by selectively energizing or non-energizing different subsets of coils belonging to the plurality of independently controllable coils.

14. The method of claim 13, further comprising varying either the point of opposition, the gap, or both during a treatment session by selectively energizing or non-energizing different subsets of coils belonging to the independently controllable coils across multiple pulses, wherein different subsets of the independently controllable coils are energized for different pulses with a pause between at least some of the pulses during which no coils are energized.

15. The method of claim 12, further comprising providing the treatment zone shaped to receive a human foot with a proximal opening and inserting the human foot into the treatment zone through the proximal opening without manual grasping or assistance.

16. The method of claim 12, wherein the coils are configured in a multi-tap configuration.

17. A magnetic pulse therapy device for treating a human foot, comprising:
    an applicator having a cavity shaped to receive at least a portion of a human foot, accessible through a proximal opening;
    a segmented solenoid comprising a plurality of independently controllable coils arranged circumferentially around and longitudinally along the cavity; and
    a controller configured to selectively control the coils to produce opposing magnetic flux directions with one or more points of opposition and gaps between energized coils, thereby dynamically directing magnetic flux within the cavity to target specific areas of the foot.

18. The device of claim 17, wherein the controller is configured to:
    control a first subset of the coils to produce a first direction of the opposing magnetic flux;
    control a second subset of the coils to produce a second direction of the opposing magnetic flux; and
    form a gap by non-energizing one or more coils between the first and second subsets, thereby directing magnetic flux within the cavity to target specific areas of the foot.

19. The device of claim 17, wherein the controller is configured to vary either the points of opposition, the gaps, or a combination of both during a treatment session by selectively energizing or non-energizing different subsets of coils belonging to the plurality of independently controllable coils:
- (a) between pulses; or
- (b) throughout a pulse, during which at least one coil remains energized as the configuration of energized or non-energized coils changes one or more times, all coils belonging to the plurality of independently controllable coils;
- (c) or both (a) and (b).

20. The device of claim 17, wherein the controller is configured to execute a treatment protocol, and the treatment protocol is selected by one or more of:
- (a) a user choosing from a selection of pre-programmed treatment protocols;
- (b) the user modifying protocol parameters through a control panel or an app to modify a treatment protocol's session duration, treatment area zones, intensity, or objectives; and
- (c) a provider selecting the treatment protocol.

21. The device of claim 17, wherein subsets of coils belonging to the plurality of independently controllable coils may have different treatment protocols.

22. The device of claim 17, wherein at least some of the coils are configured in a multi-tap configuration.

23. The device of claim 17, wherein the proximal opening is configured to allow insertion and removal of the human foot by sliding the human foot laterally into the cavity without navigating around obstructions.

24. A magnetic therapy device comprising:
- a segmented solenoid having multiple independently controllable coils;
- a controller configured to energize the multiple coils to deliver magnetic pulses to an appendage positioned within a core of the segmented solenoid during a treatment session; and
- a treatment zone defined as the longitudinal span between the outermost energized coils in the segmented solenoid in a during the treatment session, wherein the controller is configured according to a treatment protocol to produce oriented magnetic flux within the treatment zone by at least one of the following techniques:
  - (a) energizing a first subset of the multiple coils to generate flux in a first direction and a second subset of the coils to generate flux in an opposing direction, thereby creating a point of opposition and a gap allowing magnetic flux to escape laterally;
  - (b) selectively energizing or deenergizing subsets of the coils within the treatment zone to control flux distribution across multiple pulses; or
  - (c) energizing one or more coils within the treatment zone at a power level different from that of an adjacent coil.

25. The device of claim 24,
wherein the treatment protocol varies the oriented magnetic flux during a treatment session:
- (a) between pulses or
- (b) throughout a pulse, during which at least one coil remains energized as the configuration of energized coils changes one or more times;
- (c) or both (a) and (b).

26. The device of claim 24, wherein the device periodically energizes different coil subsets within the treatment zone, thereby adjusting a location or presence of flux escape zones within the treatment zone.

27. The device of claim 24, wherein different treatment protocols are performed within a single treatment session.

28. The device of claim 24, wherein a treatment protocol can provide separate parameters for zones within the segmented solenoid, wherein each zone within the segmented solenoid is a subset of coils within the treatment zone.

29. The device of claim 24, wherein the controller is configured to energize and deenergize at least some of the coils within the treatment zone in a pre-determined pattern, the pattern controlling at least one of an activation sequence, a timing, or a polarity of the multiple coils to create a dynamic effect across the treatment zone.

30. The device of claim 24, wherein at least some of the coils are configured in a multi-tap configuration.

* * * * *